United States Patent
Varga et al.

(10) Patent No.: US 9,439,803 B2
(45) Date of Patent: Sep. 13, 2016

(54) PATIENT WARMING DEVICE WITH PATIENT ACCESS

(71) Applicant: CareFusion 2200, Inc., San Diego, CA (US)

(72) Inventors: Christopher M. Varga, Laguna Hills, CA (US); Michael McMahon, Yorba Linda, CA (US); Thomas Dillingham, Aliso Viejo, CA (US); James Chan, San Marino, CA (US); Todd Schmaltz, San Diego, CA (US); Karthikeyan Rajendran, Woodridge, IL (US)

(73) Assignee: CareFusion 2200, Inc., San Diego, CA (US)

( * ) Notice: Subject to any disclaimer, the term of this patent is extended or adjusted under 35 U.S.C. 154(b) by 236 days.

(21) Appl. No.: 13/801,512

(22) Filed: Mar. 13, 2013

(65) Prior Publication Data

US 2014/0277301 A1    Sep. 18, 2014

(51) Int. Cl.
*A61F 7/02* (2006.01)
*A61F 7/00* (2006.01)

(52) U.S. Cl.
CPC .......... *A61F 7/02* (2013.01); *A61F 2007/0029* (2013.01); *A61F 2007/0031* (2013.01); *A61F 2007/0034* (2013.01);
(Continued)

(58) Field of Classification Search
CPC ............. A61F 2007/0004; A61F 7/02; A61F 2007/0001; A61F 7/03; A61F 2007/0242; A61F 2007/026; A61F 2007/0045; A61F 7/10; A61F 2007/0036; A61F 2007/0292; A61F 7/103; A61F 2007/0009

USPC .................................................. 607/96–114
See application file for complete search history.

(56) References Cited

U.S. PATENT DOCUMENTS

| 4,029,087 A | 6/1977 | Dye et al. |
| 4,149,529 A | 4/1979 | Copeland et al. |

(Continued)

FOREIGN PATENT DOCUMENTS

| WO | 2014/158461 A1 | 10/2014 |
| WO | 2014/158463 A1 | 10/2014 |

OTHER PUBLICATIONS

International Search Report mailed on May 12, 2014 in PCT/US2014/016934.
(Continued)

*Primary Examiner* — Joseph Stoklosa
*Assistant Examiner* — Adam Avigan
(74) *Attorney, Agent, or Firm* — McDermott Will & Emery LLP

(57) ABSTRACT

A patient warming device with patient access for maintaining normothermia and/or treating hypothermia is provided. The device includes a first compliant layer and a second compliant layer sealed together around an outer border to contain a liquid between the two layers and to form a wrap that surrounds and conforms to a body portion of a patient. A plurality of flaps extends from opposite sides of a generally longitudinal central portion of the wrap, such that one or more flaps from the opposite sides fasten to each other to surround the body portion. The flaps are openable during functional use to provide access to an underlying patient body surface. A continuous fluid flow path extends between the first compliant layer and the second compliant layer between a fluid inlet and a fluid outlet to carry liquid and deliver heat through the wrap.

13 Claims, 17 Drawing Sheets

(52) U.S. Cl.
CPC .............. *A61F 2007/0036* (2013.01); *A61F 2007/0037* (2013.01); *A61F 2007/0039* (2013.01); *A61F 2007/0043* (2013.01); *A61F 2007/0045* (2013.01); *A61F 2007/0054* (2013.01); *A61F 2007/0215* (2013.01); *A61F 2007/0217* (2013.01); *A61F 2007/0219* (2013.01); *A61F 2007/0228* (2013.01); *A61F 2007/0231* (2013.01); *A61F 2007/0268* (2013.01); *A61F 2007/0273* (2013.01); *A61F 2007/0274* (2013.01); *A61F 2007/0288* (2013.01)

(56) References Cited

U.S. PATENT DOCUMENTS

| | | | |
|---|---|---|---|
| 4,624,244 A | | 11/1986 | Taheri |
| 4,753,240 A * | | 6/1988 | Sparks .......................... 607/108 |
| 4,854,319 A * | | 8/1989 | Tobin ........................... 607/109 |
| 4,962,761 A | | 10/1990 | Golden |
| 5,074,285 A * | | 12/1991 | Wright .......................... 607/111 |
| 5,409,500 A * | | 4/1995 | Dyrek .......................... 607/111 |
| 5,411,541 A | | 5/1995 | Bell et al. |
| 5,411,542 A * | | 5/1995 | Jensen ......................... 607/104 |
| 5,496,357 A | | 3/1996 | Jensen et al. |
| D383,848 S | | 9/1997 | Mason et al. |
| 5,683,438 A | | 11/1997 | Grahn |
| 5,800,383 A | | 9/1998 | Chandler et al. |
| 5,830,180 A | | 11/1998 | Chandler et al. |
| 5,904,710 A | | 5/1999 | Davis et al. |
| 6,024,720 A | | 2/2000 | Chandler et al. |
| 6,500,200 B1 * | | 12/2002 | Kushnir ........................ 607/104 |
| 6,692,518 B2 | | 2/2004 | Carson |
| 6,743,250 B2 | | 6/2004 | Renfro |
| 6,846,322 B2 | | 1/2005 | Kane et al. |
| 7,044,924 B1 | | 5/2006 | Roth et al. |
| 7,160,316 B2 | | 1/2007 | Hamilton et al. |
| 7,354,411 B2 | | 4/2008 | Perry et al. |
| 8,066,752 B2 | | 11/2011 | Hamilton et al. |
| 8,182,521 B2 | | 5/2012 | Kane et al. |
| 8,394,042 B1 | | 3/2013 | Mirza |
| 2003/0149461 A1 * | | 8/2003 | Johnson ........................ 607/108 |
| 2004/0010212 A1 | | 1/2004 | Kuiper et al. |
| 2004/0068310 A1 | | 4/2004 | Edelman |
| 2005/0070828 A1 | | 3/2005 | Hampson et al. |
| 2006/0178717 A1 | | 8/2006 | Harris et al. |
| 2007/0162096 A1 | | 7/2007 | Zakuto et al. |
| 2008/0021531 A1 | | 1/2008 | Kane et al. |
| 2008/0064992 A1 | | 3/2008 | Stewart et al. |
| 2008/0132816 A1 | | 6/2008 | Kane et al. |
| 2008/0132976 A1 | | 6/2008 | Kane et al. |
| 2009/0069731 A1 | | 3/2009 | Parish et al. |
| 2009/0177184 A1 | | 7/2009 | Christensen et al. |
| 2009/0228082 A1 * | | 9/2009 | Ross et al. .................... 607/107 |
| 2010/0081974 A1 | | 4/2010 | Vess |
| 2010/0210982 A1 | | 8/2010 | Balachandran et al. |
| 2011/0098792 A1 | | 4/2011 | Lowe et al. |
| 2011/0152983 A1 | | 6/2011 | Schirrmacher et al. |
| 2011/0172749 A1 | | 7/2011 | Christensen et al. |
| 2012/0078147 A1 | | 3/2012 | Ogulnick et al. |
| 2012/0130457 A1 | | 5/2012 | Gammons et al. |
| 2012/0185021 A1 * | | 7/2012 | Johnson et al. ............. 607/104 |
| 2012/0316480 A1 | | 12/2012 | Nolan et al. |
| 2013/0030331 A1 | | 1/2013 | Quisenberry et al. |
| 2014/0222121 A1 | | 8/2014 | Spence et al. |

OTHER PUBLICATIONS

International Search Report mailed on May 12, 2014 in PCT/US2014/016956.

3M Infection Prevention Solutions, "3M™ Bair Hugger™ Therapy," Arizant Healthcare, Inc., a 3M Company, Eden Prairie, MN, 2011, 2 pages.

Smiths, "Snuggle Warm® Sterile Cardiac Blanket," Smiths Medical ASD, Inc., Anesthesia and Safety Devices Division, Rockland, MA, 2004, 2 pages.

Smiths Medical, "Snuggle Warm® Pediatric Underbody Blankets," Smiths Medical ASD, Inc., Rockland, MA, 2007, 2 pages.

Stryker Medical, "Medi-Therm®—Precise. Easy. Versatile.," Medi-Therm Hyper/Hypothermia System, Gaymar Industries, Orchard Park, NY. http://www.stryker.com/en-us/GSDAMRetirement/index.htmstellent/groups/public/documents/web_content/med_medi-therm_brochure_rev_c.pdfm Retrieved online Dec. 6, 2012, 6 pages.

Stryker Medical, "Temperature Management Solutions," Gaymar Industries, Orchard Park, NY, 2011, 4 pages.

Stryker, "T/Pump® Localized Therapy—Safe and Effective Localized Warming and Cooling Therapy," Gaymar Industries, Orchard Park, NY, 2011, 2 pages.

International Search Report and Written Opinion issued in PCT/US2014/16916, dated Jul. 11, 2014.

Ozbayrak, N et al., The Effects of Inlay Yarn Amount and Yarn Count on Extensibility and Bursting Strength of Comparison Stocking, Journal of Textile and Apparel/Tekstil ve Konfeksiyon, 2009, vol. 19, No. 2, pp. 102-107.

* cited by examiner

PATIENT WARMING DEVICE WITH PATIENT ACCESS

TECHNICAL FIELD

Embodiments disclosed in the present application relate generally to patient warming devices embodied as wraps for maintaining normothermia and/or treating hypothermia.

BACKGROUND

During surgical procedures, patients may be placed under anesthesia. As a result, the body's natural thermoregulatory mechanisms may be affected and systemic vasodilation may occur. Systemic dilation counteracts the body's natural heat retention mechanism and allows body heat to flow down a concentration gradient to the extremities, where heat is lost to the environment. As a result, the patient is at risk of perioperative hypothermia. Medical complications may result from perioperative hypothermia and may include peri-operative and post-operative complications, including for example, increased wound infection rates, metabolic acidosis, respiratory distress, cardiovascular effects, surgical bleeding, and increased risk of mortality. Therefore, a need exists for patient warming devices that actively warm the patient to maintain normothermia, prevent perioperative hypothermia, and/or treat hypothermia.

Forced air convective warming blankets, large wraps, or pads are commonly used to cover various parts of the body. These warming devices generally cover a large portion of the body, restricting access to the patient in covered areas. A surgeon, or other medical staff, requiring access to the covered portions of the body in order to introduce surgical elements, such as intravenous feed lines, pulse oximetry probes, needles, vitals monitoring instruments, and other medical instruments, may need to reposition or remove the warming device. Removal and repositioning of the device not only increases the time required for the surgical procedure, but may also significantly reduce heat transfer to the patient during that time. Moreover, control systems for forced air convective devices tend to generate loud noise that may distract or interfere with communication between surgeons and medical personnel in an operating room.

Active warming devices also tend to cause stippling on patients' skin. Stippling may cause pain in geriatric or elderly patients, pediatric or very young patients, or patients with sensitive skin. Stippling is also unsightly, and may evoke unnecessary concern from a patient and from friends and family members who observe the stippling on the patient's skin.

Deep vein thrombosis (DVT) is another common concern during surgical operations. Compression devices are commonly used to prevent deep vein thrombosis by applying intermittent pneumatic compression to a patient's lower extremities, such as the legs and feet of a patient. The intermittent pressure promotes venous blood flow so as to prevent deep vein thrombosis. DVT prevention devices may use negative pressure, or vacuum pressure, to apply compression, which requires a seal around the patient's extremity and does not allow for access to the underlying surface of the patient. Applying negative pressure, or vacuum pressure, for DVT prevention also tends to increase stippling.

During surgical procedures, it is common to use a device for preventing deep vein thrombosis and a separate device for active patient warming on different body portions of the patient. For example, a device for preventing deep vein thrombosis may be attached to the patient's leg, while a device for active patient warming may be attached to another part of the patient's body. Therefore, there is a need and/or desire in the art to provide devices and methods for patient care that will promote and maintain normothermia and/or treat hypothermia while providing access to portions of the patient's body underlying the device, preventing deep vein thrombosis, and avoiding or minimizing stippling, impressed wrinkles, or the like on a patient's skin.

BRIEF SUMMARY

In one aspect, a patient warming device with patient access is provided for maintaining normothermia and/or treating hypothermia. The device includes a first compliant layer and a second compliant layer sealed together around an outer border to contain a liquid between the two layers and to form a wrap that surrounds and conforms to a body portion of a patient. The wrap includes a generally longitudinal central portion sized to cover a surface of the body portion. A plurality of flaps extends from opposite sides of the central portion, such that one or more flaps from the opposite sides fasten to each other to surround the body portion. The flaps are openable during functional use to provide access to an underlying patient body surface. A continuous fluid flow path extends between the first compliant layer and the second compliant layer between a fluid inlet and a fluid outlet. The continuous fluid flow path is defined by the outer border and a plurality of internal sealed connections between the first and second compliant layers.

In another aspect, a method for warming a patient to maintain normothermia and/or treat hypothermia is provided. The method includes wrapping an appendage of the patient in a patient warming device. The patient warming device includes a first compliant layer and a second compliant layer sealed together around an outer border to contain a liquid between the two layers. A generally longitudinal central portion of the patient warming device is aligned along an underside of the appendage. A first set of flaps extending from a first side of the central portion is folded around a topside of the appendage. A second set of flaps extending from a second side opposite the first side of the central portion is folded around the topside of the appendage. The first set of flaps and the second set of flaps are fastened to each other such that the first compliant layer makes skin contact with the appendage. The method further includes directing the liquid, via a fluid inlet of the patient warming device, into a continuous fluid flow path that extends between the first compliant layer and the second compliant layer. The fluid flow path guides the liquid through the central portion, the first set of flaps, and the second set of flaps so as to maintain normothermia or treat hypothermia in the patient.

In another aspect, a patient warming device for maintaining normothermia and/or treating hypothermia is provided. The patient warming device includes a first compliant layer and a second compliant layer sealed together around an outer border to contain a liquid between the two layers and to form a wrap that surrounds and conforms to an appendage of a patient. The wrap includes a generally longitudinal central portion sized to cover a surface of the appendage. A continuous fluid flow path extends between the first compliant layer and the second compliant layer between a fluid inlet located at a distal end of a first side of the central portion and a fluid outlet located at a distal end of a second side of the central portion opposite the first side. The continuous fluid flow path is defined by the outer border and a plurality of internal sealed connections between the first and second compliant layers. The wrap further includes a first set of flaps and a second set of flaps. The first set of flaps extends from the first side of the central portion, and the fluid flow path leads from the fluid inlet to the first set of flaps. The second set of flaps extends from the second side of the central portion, and the fluid flow path leads from the first set of flaps to the second set of flaps to the fluid outlet. A first pair of flaps includes a flap nearest the distal end from each of the first set of flaps and the second set of flaps. The first pair of flaps extends to a first distance from the central portion. A second pair of flaps includes a flap nearest a proximal end of the central portion from each of the first set of flaps and the second set of flaps. The second pair of flaps extends to a second distance, greater than the first distance, from the central portion. The wrap further includes a plurality of hook and loop fasteners, including hook or loop components affixed to the first compliant layer of the first set of flaps; and corresponding hook or loop components affixed to the second compliant layer of the second set of flaps.

Other systems, methods, features, and advantages of the disclosure will be, or will become, apparent to one with skill in the art upon examination of the following figures and detailed description. It is intended that all such additional systems, methods, features and advantages be included within this description, be within the scope of the invention, and be protected by the claims.

DETAILED DESCRIPTION

Figure 1:
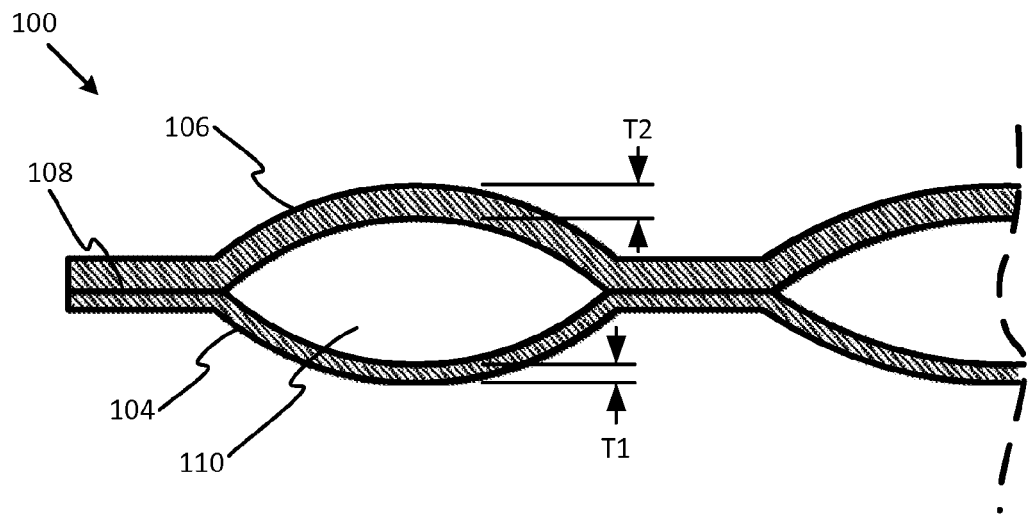
FIG. 1 is a cross sectional view of an exemplary patient warming device with patient access.

Commonly owned U.S. application Ser. Nos. 13/801,270 and 13/801,334 entitled, respectively, "Compressive Patient Warming Device" and "Patient Warming and Deep Vein Thrombosis Prevention System," are being filed concurrently herewith, and each is incorporated herein by reference in its entirety. Various embodiments are described below with reference to the drawings in which like elements generally are referred to by like numerals. The relationship and functioning of the various elements of the embodiments may better be understood by reference to the following detailed description. However, embodiments are not limited to those illustrated in the drawings. It should be understood that the drawings are not necessarily to scale, and in certain instances details may have been omitted that are not necessary for an understanding of embodiments disclosed herein, such as—for example —conventional fabrication and assembly. The invention is defined by the claims, may be embodied in many different forms, and should not be construed as limited to the embodiments set forth herein; rather, these embodiments are provided so that this disclosure will be thorough and complete, and will fully convey enabling disclosure to those skilled in the art. As used in this specification and the claims, the singular forms "a," "an," and "the" include plural referents unless the context clearly dictates otherwise.

A patient warming device with patient access and a patient warming method are provided in some embodiments. The patient warming device includes a first compliant layer and a second compliant layer that are sealed together around an outer border to contain a liquid between the two layers. The layers form a wrap that surrounds and conforms to a body portion, appendage, or extremity of a patient so as to maintain normothermia of the patient or to treat hypothermia. As used herein, normothermia is defined as a range of body core temperature between about 36.5° C. to 37.5° C.±0.5° C. (about 97.7° F. to 99.5° F.±0.9°). Hypothermia is defined as a core temperature less than about 36° C. (about 96.8° F.). Mild hypothermia is defined as ranging from about 1° C. to 2° C. (about 1.8° F. to 3.6° F.) below body core temperature, while moderate hypothermia constitutes a body core temperature of about 35° C. (about 95° F.), and severe hypothermia is a body core temperature below 35° C.

The wrap may include a generally longitudinal central portion that is sized to cover a surface of the body portion, or appendage, of the patient. A plurality of flaps may extend from one or more sides of the central portion and fasten to each other to surround the body portion, or appendage, of the patient. A continuous fluid flow path may extend between the first and second compliant layers. The fluid flow path may be defined by the outer border and a plurality of internal sealed connections between the first and second compliant layers. The fluid flow path may guide a liquid, such as a warm or heated liquid (e.g., water or other aqueous liquids, a viscous gel, a hydrogel, an organic liquid (e.g., oil or oil-based liquid, or any other organic liquid or flowable material with a heat capacity suitable for effective use in keeping with the principles of the present disclosure), a synthetic oil, a foam, or any combination thereof), through the flaps and central portion of the wrap so as to substantially fill the wrap.

In some embodiments, a patient warming method includes wrapping a body portion, appendage, or extremity of a patient in a patient warming device that includes a first compliant layer and second compliant layer sealed together around an outer border to contain a liquid between the two layers. A generally longitudinal central portion of the patient warming device is aligned along an underside of the appendage. A first set of flaps extending from a first side of the central portion is folded around the topside of the appendage. A second set of flaps extending from a second side opposite the first side of the central portion is folded around the topside of the appendage. The first and second sets of flaps are fastened to each other such that the first compliant layer makes skin contact with the appendage. The liquid is directed, via a fluid inlet of the patient warming device, into a continuous fluid flow path extending between the first compliant layer and the second compliant layer. The fluid flow path guides the liquid through the central portion, the first set of flaps, and the second set of flaps.

As used herein, the term "underside" means any surface area of the patient's skin that is in contact with the central portion of the patient warming device, and does not limit the use of the patient warming device to any particular orientation. For example, the "underside" of a hand may mean the palm of the hand or the back of the hand, whichever is in contact with the central portion of the patient warming device. As used herein, the term "topside" means any surface area of the patient's skin that is in contact with flaps of the patient warming device, and does not limit the use of the patient warming device to any particular orientation. For example, the "topside" of a lower leg may mean a calf or a shin, whichever is in contact with flaps of the patient warming device. As another example, the palm and inner forearm are referred to as the "underside" when the patient warming device is aligned on a patient so that the palm and inner forearm of the patient lies on, or is in contact with, the central portion of the patient warming device. In this example, the back of the hand and outer forearm are referred to as the "topside."

The disclosed patient warming device may be prepackaged as a disposable or reusable unit for use in surgical environments. Prepackaging may include any necessary sanitization of all components of the device. Prepackaging may also include "seeding" the device with a disinfectant agent, for example, at the fluid inlet so that the liquid carries the agent through the device and an attached pump system. Materials used may include medical grade materials that are antimicrobial, anti-infective, anti-biofilm, disinfecting, decontaminating and/or are embedded with antimicrobial, anti-infective, anti-biofilm, disinfecting or decontaminating materials.

The disclosed patient warming device and method may maintain normothermia or treat hypothermia in a patient whose thermoregulatory mechanisms are affected by a health condition, anesthesia, or other causes, by surrounding about 5% to about 10% of a patient's external surface area with a wrap that is substantially filled with a heat transferring liquid. Liquid, such as water, is a preferred heat transferring medium because it is readily available, has superior heat transfer properties relative to gas or air, and because operation of fluid control pumps for liquids creates less noise than for forced air systems. One of skill in the art would recognize, however, that the patient warming devices and methods disclosed herein may also be used with any suitable fluid, including, for example, forced air.

In addition to actively warming the patient by delivering heat through a wrap in contact with the patient's skin, some embodiments of the patient warming device may apply a predetermined compressive load, or pressure, to the surrounded body portion, or appendage, so as to facilitate increased local blood flow. The compressive load, or pressure, may be applied statically or in pulses. When the compressive load is applied in pulses, the pressure may alternate between a higher pressure and a lower pressure, between a high pressure and zero pressure, or between a positive pressure and a negative/vacuum pressure. The compressive load may be applied evenly over the surface of the surrounded body portion or concentrated at predetermined locations along the surrounded body portion. Applying a compressive load in combination with heat delivery may increase blood flow and decrease the amount of time required to warm the patient.

A compressive patient warming device may include an inner layer and an outer layer. The inner garment may be an elastic inner layer that conforms snugly to the shape of an appendage, or body portion, of the patient so that the inner layer wraps around and substantially contacts most of an underlying surface area of the appendage. The outer layer is attached to and covers the inner layer to form a space that holds a heat transfer medium between the inner and outer layers while the inner layer is wrapped around the appendage. The compressive patient warming device may simultaneously deliver heat and apply a predetermined compressive load to the surrounded appendage so as to maintain normothermia and/or treat hypothermia in the patient.

In some embodiments, a method for warming and applying compressive force on the appendage includes inserting the appendage into an elastic inner layer of a compressive patient warming device. The inner layer conforms snugly to the irregular shape of the appendage so that the inner layer wraps around and substantially contacts most of an underlying surface area of the appendage. A predetermined compressive load is applied to an outer layer that adjoins the inner layer. A space is formed between the inner and outer layers to hold a heat transfer medium. The predetermined compressive load applies pressure to the appendage through the heat transfer medium and the inner layer.

Prevention of deep vein thrombosis (DVT) may be achieved using the disclosed patient warming device by applying intermittent pressure to the liquid in the fluid flow path and using a valve system and/or a single-channel or multi-channel fluid pump system. Alternatively, the patient warming device may be configured with an inflatable layer that is in communication with an air pump. The inflatable layer is partially or fully concentric with the first and second compliant layers of the patient warming device when the wrap surrounds a body portion of the patient. The air in the inflatable layer remains separate from the liquid between the first and second compliant layers.

In some embodiments, a patient warming and deep vein thrombosis prevention system includes a first compliant layer and a second compliant layer sealed together around an outer border to contain a warm liquid between the two layers. As used herein, a "warm liquid" means a liquid provided at a temperature of at least about ambient temperature, or 20° C. (68° F.), to about 41° C. (105.8° F.). Ambient temperature may be the temperature of the environment surrounding the patient, and therefore, may vary with the surrounding environment. The layers form a wrap that surrounds and conforms to a body portion of a patient. The wrap includes a generally longitudinal central portion sized to cover a surface of the body portion. A plurality of flaps extends from opposite sides of the central portion. One or more flaps from the opposite sides fasten to each other to surround the body portion and the flaps are openable during functional use to provide access to an underlying patient body surface. A continuous fluid flow path extends between the first compliant layer and the second compliant layer between a fluid inlet and a fluid outlet. The fluid flow path is defined by the outer border and a plurality of internal sealed connections between the first and second compliant layers. A fluid control pump is connected to the wrap to direct the liquid through the fluid flow path so as simultaneously to inflate the wrap and apply pressure and heat to the body portion being surrounded by the wrap.

In some embodiments, a method for patient warming and prevention of deep vein thrombosis using the patient warming and deep vein thrombosis system may be provided. The method includes fastening a first pair of flaps of the plurality of flaps to surround an upper portion of the shin. A second pair of flaps of the plurality of flaps is fastened to surround a lower portion of the shin. A third pair of flaps of the plurality of flaps is fastened to surround the foot of the patient. The pump is activated to fill the fluid flow path with warm liquid sufficiently to exert surface pressure on the patient. The pressure is provided at a level generally effective to prevent deep vein thrombosis.

In some embodiments, a method for patient warming and prevention of deep vein thrombosis may be provided. The method includes wrapping an appendage of a patient in a wrap comprising a first compliant layer and a second compliant layer sealed together around an outer border to contain a liquid between the two layers. The appendage is positioned on a generally longitudinal central portion of the wrap so that substantially most, or substantially all (e.g., about 90% to 95%), of the central portion is in contact with a surface of the appendage. The appendage is enclosed in the wrap by fastening a plurality of flaps around the appendage. The plurality of flaps extends from the central portion of the wrap and is defined by the outer border of the wrap. The wrap is filled, via a fluid inlet that is at a distal end of the central portion of the wrap, with a warm liquid sufficiently to exert a surface pressure on the patient. The surface pressure is provided at a level generally effective to prevent deep vein thrombosis and the warm liquid is provided at a temperature that is generally effective to maintain normothermia or treat hypothermia.

With reference to FIGS. 1-5, some embodiments of the patient warming device with patient access 100 may include a wrap 102 formed from a first compliant layer 104 and a second compliant layer 106 sealed together around an outer border 108, or outer edges, to contain a liquid 110 between the layers 104, 106. The first and second compliant layers 104, 106 may be, for example, PVC, urethane, polyurethane, polyethylene (PE), ethylene-vinyl acetate (EVA), EVA/PE blends or copolymers, styrenic block copolymers (SBC), medical elastomers, olefin-based compounds, acrylonitrile butadiene styrene (ABS), or any other material that is sufficiently non-permeable, flexible, and thin so as to be suitable for containing liquid and conforming to a body portion or appendage of a patient. The first and second layers 104, 106 may be sealed around the border 108, for example, by radio frequency (RF) welding, so as to contain the liquid. Other plastic welding techniques, such as hot gas welding, head sealers, speed tip welding, contact welding, hot plate welding, ultrasonic welding, friction welding, laser welding, or any other known techniques may be used to seal the first and second layers 104, 106 together. The first and second layers 104, 106 may alternatively be adhesively bonded. Alternatively, the first and second layers 104, 106 may be partially sealed together, by RF welding or other plastic welding techniques, to allow for a heat transfer media (e.g., memory foam, heat transfer liquid or gel, sand, or heat transferring beads) to be inserted between the layers. The first and second layers 104, 106 may be made from the same material, or different material, or a combination of different materials. The liquid may be water or other aqueous liquids, a viscous gel, an organic liquid (e.g., oil or oil-based liquid, or any other organic liquid or flowable material with a heat capacity suitable for effective use in keeping with the principles of the present disclosure), a synthetic oil, a foam, or any combination thereof, or any other liquid that has appropriate heat transfer qualities, e.g. high heat capacity and high thermal conductivity, to deliver heat quickly and efficiently to the patient.

The first compliant layer 104 may be configured to contact the skin of the patient, and the second compliant layer 106 may face away from the skin, or be exposed to the surrounding environment. Because first compliant layer 104 is in contact with the skin of the patient, it may be desirable for the first compliant layer 104 to be thinner and/or more skin-conformingly compliant than the second compliant layer 106 so as to provide more efficient heat transfer to the patient. Because second compliant layer 106 is exposed to the surrounding environment, it may have a greater thickness and/or insulating properties so as to reduce heat loss to the surrounding environment.

With reference to FIG. 1, for example, the first compliant layer 104 may have a thickness T1 that is approximately 50% or less of the thickness T2 of the second compliant layer 106. Alternatively, the first compliant layer 104 may have any thickness that is less than the thickness, the same thickness, or a greater thickness than the thickness T2 of second compliant layer 106.

In some embodiments, the first compliant layer 104 has a thickness T1 of about 0.004 inch (about 0.10 mm) to about 0.006 inch (about 0.15 mm) and the second compliant layer 106 has a thickness T2 of about 0.009 inch (0.22 mm) to about 0.011 inch (0.28 mm). In other embodiments, the thicknesses T1, T2 may be the same. For example, the thicknesses T1, T2 may each be 0.009 inch (0.22 mm) to 0.011 inch (0.28 mm). The thicknesses T1, T2 of the first and second compliant layers 104, 106 may vary depending on the material of the layers and intended functional use of the patient warming device.

As used herein, the term "functional use" means during operation of the device where a fluid is being moved therethrough to treat a patient. Functional use of the patient warming device may include, for example, wrapping a body portion, or appendage of the patient, in the device during an operative procedure so as to maintain normothermia or treat hypothermia in the patient while the patient is under anesthesia and undergoing a surgical procedure. For example, for use with patients who have greater heat sensitivity (e.g., elderly or very young patients) the first compliant layer 104 may be configured to have a greater thickness than for use with patients who have less heat sensitivity. As another example, a patient warming device configured for use on a patient's foot and leg may have a first compliant layer 104 with a greater thickness than for a patient warming device configured for use with areas that are generally more heat sensitive, such as a patient's hand, arm, or abdominal area. Other functional uses of the patient warming device are contemplated, such as patient comfort heating, general heat therapy and/or joint therapy.

Figure 2:
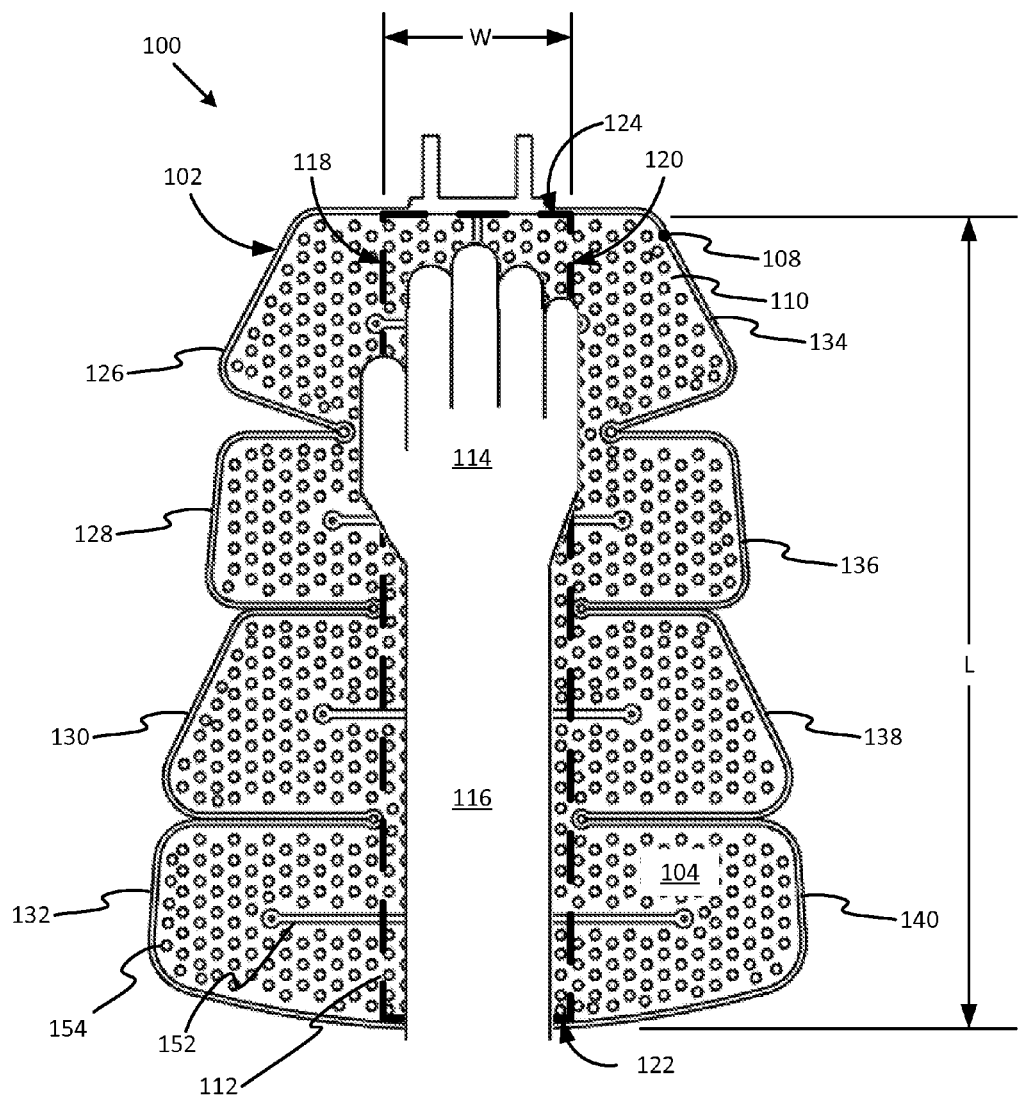
FIG. 2 is a view of an exemplary patient warming device with patient access aligned with a hand and a lower arm.

The wrap 102 may include a generally longitudinal central portion 112 that is sized to cover a surface or skin of the body portion of a patient. As shown in FIG. 2, for example, the central portion 112 may have a length L and width W that is anatomically proportionate to the length and width of a hand 114 and forearm 116 of an average human male or female adult or child. The central portion may be aligned to contact an underside of a body portion, such as the palm of the hand 114 and inside of forearm 116. Alternatively, the central portion 112 may be sized to fit an upper arm (such as around biceps and/or triceps), a hand, a lower leg (such as a calf and/or shin), an upper leg (such as a thigh) of a patient, a torso, a chest, an abdominal area, or any portion thereof, any other body portion of the patient, or any combination thereof.

A plurality of flaps may extend from a first side 118 or a second side 120 of the central portion, or from a proximal end 122 or a distal end 124 of the central portion. For example, flaps 126, 128, 130, 132 may extend from the first side 118 of the central portion 112, and flaps 134, 136, 138, 140 may extend from the second side 120 of the central portion 112. Flaps on opposite sides of the central portion 112 may correspond in size, shape and position along the central portion 112. Alternatively, flaps extending from one side of the central portion, or the first side 118, may differ in size, shape, and/or position along the central portion than flaps extending from an opposite side of the central portion, or the second side 120. In other embodiments, flaps may extend only from one side or one end of the central portion, or from one side and one end of the central portion 112, or any combination of sides and ends of the central portion 112.

Flaps extending from opposite sides of the central portion 112 may fasten to each other to surround a body portion of the patient. Alternatively, flaps may extend from one side of the central portion 112 and fasten to another side of the central portion 112. The flaps may be fastened by any suitable fastener, including, for example, hook and loop fasteners, adhesive tabs, buttons, snaps, or press and seal fasteners.

In some embodiments, when the wrap 102 is used to cover a hand 114 and forearm 116, the flaps 126, 134 located at or near the distal end 124 may extend a shorter distance from the central portion than flaps 132, 140 located at or near the proximal end 122 of the central portion. Flaps 126, 134 may be configured (e.g., sized, shaped, tapered, and/or contoured) to fold over and cover the fingers of hand 114, flaps 128, 136 configured to fold over and cover the back of the hand 114, flaps 130, 138 configured to fold over and cover a lower portion of the topside of forearm 116, and flaps 132, 140 configured to fold over and cover an upper portion of the topside of forearm 116. Flaps 126, 128, 130, 132 may extend a predetermined distance from the central portion so as to completely overlap or partially overlap with flaps 134, 136, 138, 140. Alternatively, flaps 126, 128, 130, 132 and 134, 136, 138, 140 may fold over to cover a body portion without overlapping another flap. As used herein, the term "fold over" or "fold around" means to bend and conform around a body portion to be surrounded by the wrap, and does not limit use of the patient warming device to any particular orientation. For example, from a perspective looking down at the patient, the central portion 112 may be held on the topside of any body portion or appendage of the patient while the flaps may be folded to cover the underside, or the central portion 112 may be held on the side of any part of the patient and the flaps may be folded to cover the other side of that body portion or appendage.

The patient warming device 100 provides patient access to a target area of the underlying patient body surface being surrounded by the wrap 102. For example, during an operative procedure, a surgeon or other medical personnel may access a portion of the hand 114 or arm 116, such as the topside or underside, without exposing the other body portions of the patient. In some embodiments, an intravenous line may be inserted to the topside or back of hand 114 or accessed on the back of the hand 114 by unfastening, opening, or unfolding a pair of flaps 128, 136, while the other flaps remain covering the fingers, and lower and upper forearm of the patient. Alternatively, access to the back of the hand may be provided by unfolding only one of flap 128 and/or flap 136 while the other flaps remain in contact with the patient's skin. In a similar way, access to the fingers may be provided by unfastening, opening, or unfolding, one or both of flaps 126, 134, access to the lower forearm may be provided by unfastening one or both of flaps 130, 138, and access to the upper forearm may be provided by unfastening one or both of flaps 132, 140. In some embodiments, intravenous lines and/or pulse oximeter probes may be accessed on either the hand 114 or arm 116 by unfastening, opening, or unfolding one or more of flaps 126, 134, 128, 136, 130, 138, 132, or 140 while the remaining flaps remain fastened and covering the hand 114 and the arm 116.

Providing access to a target area of the underlying patient body surface while maintaining contact with other parts of the surrounding areas increases the ability of the patient warming device 100 to maintain normothermia or treat hypothermia in the patient by maintaining heat transfer to body portions that remain covered. Also, by providing access to the target area while the wrap 102 remains in place, there is no need reposition or remove the patient warming device in order to introduce surgical elements, such as intravenous feed lines, needles, and vitals monitoring instruments. As such, it may be preferable for the flaps to be sized, shaped, and positioned so as to provide access during functional use. As described elsewhere herein, the desired access provided by the flaps will preferably be to patient surface areas used for treatment (e.g., IV sites) and/or diagnosis/monitoring (e.g., pulse oximetry monitoring).

Flaps extending from one side of the central portion 112 may correspond to flaps extending from the opposite side of the central portion 112 in size, shape, and/or location. Alternatively, flaps extending from one side of the central portion 112 do not correspond with flaps extending from the opposite side in size, shape, and/or location. For example, flaps 134, 136, 138, and 140 may each extend a distance corresponding to the distances of flaps 126, 126, 128, 130 and 132, respectively. Flaps 134, 136, 138, and 140 may each have a height corresponding to the heights of flaps 126, 126, 128, 130 and 132, respectively. Alternatively, corresponding flaps on opposite sides may extend different distances and have different heights. Additional, fewer, or different flaps may be included in the patient warming device 100.

Figure 3:
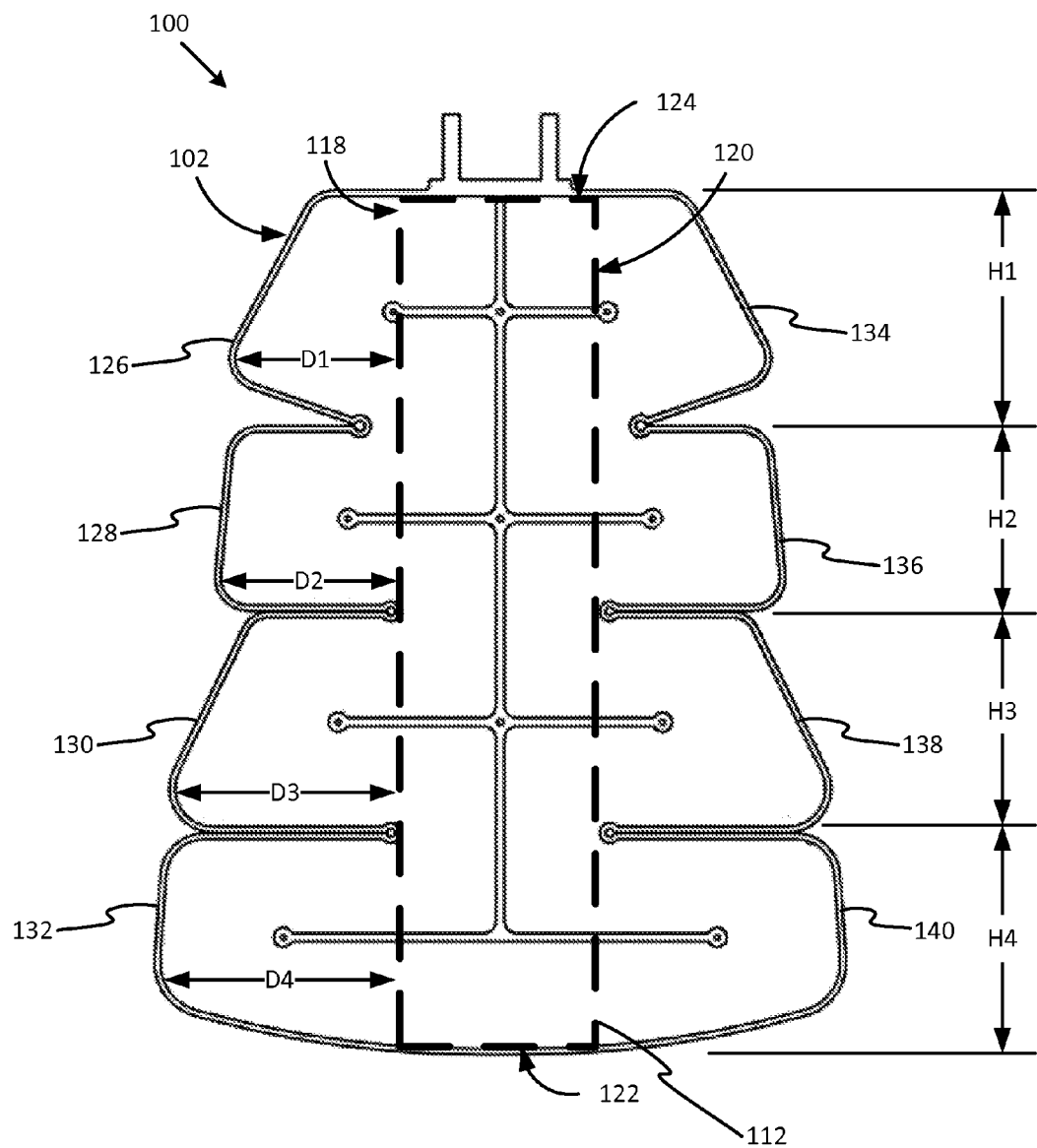
FIG. 3 is a first view of an exemplary patient warming device with patient access.

For example, as illustrated with reference to FIG. 3, flaps 126, 128, 130 and 132 may each extend a distance D1, D2, D3, and D4, respectively from the first side of the central portion 112. Flaps 134, 136, 138, and 140 may each extend a distance equal to the distance of corresponding flaps 126, 126, 128, 130 and 132, respectively. Distances D1, D2, D3, and D4, of the flaps when added to the width W of the corresponding portion of central portion 112, may be configured to fit the circumference of a predetermined body portion, or appendage, to be surrounded or covered, such as a patient's fingers, hand, lower forearm, and upper forearm, or any other part of the patient's body. In some embodiments, distance D1 may be approximately 3.0 to 4.0 inches (7.5 to 10.2 cm), distance D2 may be approximately 3.4 to 4.6 inches (8.6 to 11.7 cm), distance D3 may be approximately 4.25 to 5.75 inches (10.7 to 14.6 cm), and distance D4 may be approximately 4.4 to 6 inches (11.3 to 15.3 cm). Alternatively, flaps may extend equal distances from each side of the central portion 112. The size of the flaps may be configured to fit patients of various sizes and stature.

The flaps may be arranged contiguously along each side of the central portion 112, or the flaps may be spaced apart from each other. As shown in FIG. 3, for example, flaps 126, 128, 130 and 132 may each have a height H1, H2, H3, and H4, respectively. Heights H1, H2, H3, and H4 may correspond to the length of a predetermined body portion, or appendage, to be surrounded or covered, such as a patient's fingers, hand, lower forearm, and upper forearm, or any other part of the patient's body. In some embodiments, height H1 may be approximately 4.5 to 6.3 inches (11.8 to 16.1 cm), height H2 may be approximately 3.5 to 4.9 inches (9.0 to 12.5 cm), height H3 may be approximately 4.25 to 5.75 inches (10.7 to 14.7 cm), and height H4 may be approximately 4.25 to 5.75 inches (9.1 to 12.4 cm). The total height of the flaps may equal the overall length L of the central portion 112, or may be less than or greater than the overall length L of the central portion 112. The size of the flaps may be configured to fit patients of various sizes and stature.

In some embodiments, liquid 110 may enter the wrap 102 through fluid inlet 142 and exit through fluid outlet 144. At the fluid inlet 142, the liquid 110 may be a warm or heated liquid that is at a temperature between about ambient temperature, or about 20° C. (68° F.), to about 41° C. (105.8° F.). As the fluid travels from the fluid inlet 142 to the fluid outlet 144, the temperature of the fluid may gradually decrease, such that the temperature of fluid at the fluid outlet 144 is less than the temperature of the fluid at the fluid inlet 142. For example, the temperature of the liquid at fluid inlet 142 may be approximately 0.2° C. (32° F.) to 1.0° C. (34° F.) warmer than the temperature of the liquid at the fluid outlet 144. Fluid inlet 142 and outlet 144 may include flexible or rigid tubes, such as PVC, urethane, polyurethane, PE, EVA, EVA/PE blends or copolymers, SBC, medical elastomers, olefin-based compounds, ABS, polycarbonate. A fluid control pump may be connected to fluid inlet 142 to heat and pump the liquid 110 through a continuous fluid flow path 146. The fluid inlet 142 and fluid outlet 144 may be located on the same or separate sides or ends of the wrap 102. In some embodiments, fluid inlet 142 and/or fluid outlet 144 may include a control valve to control the flow of liquid 110 in and out of the wrap 102, or fluid flow path 146.

Figure 4:
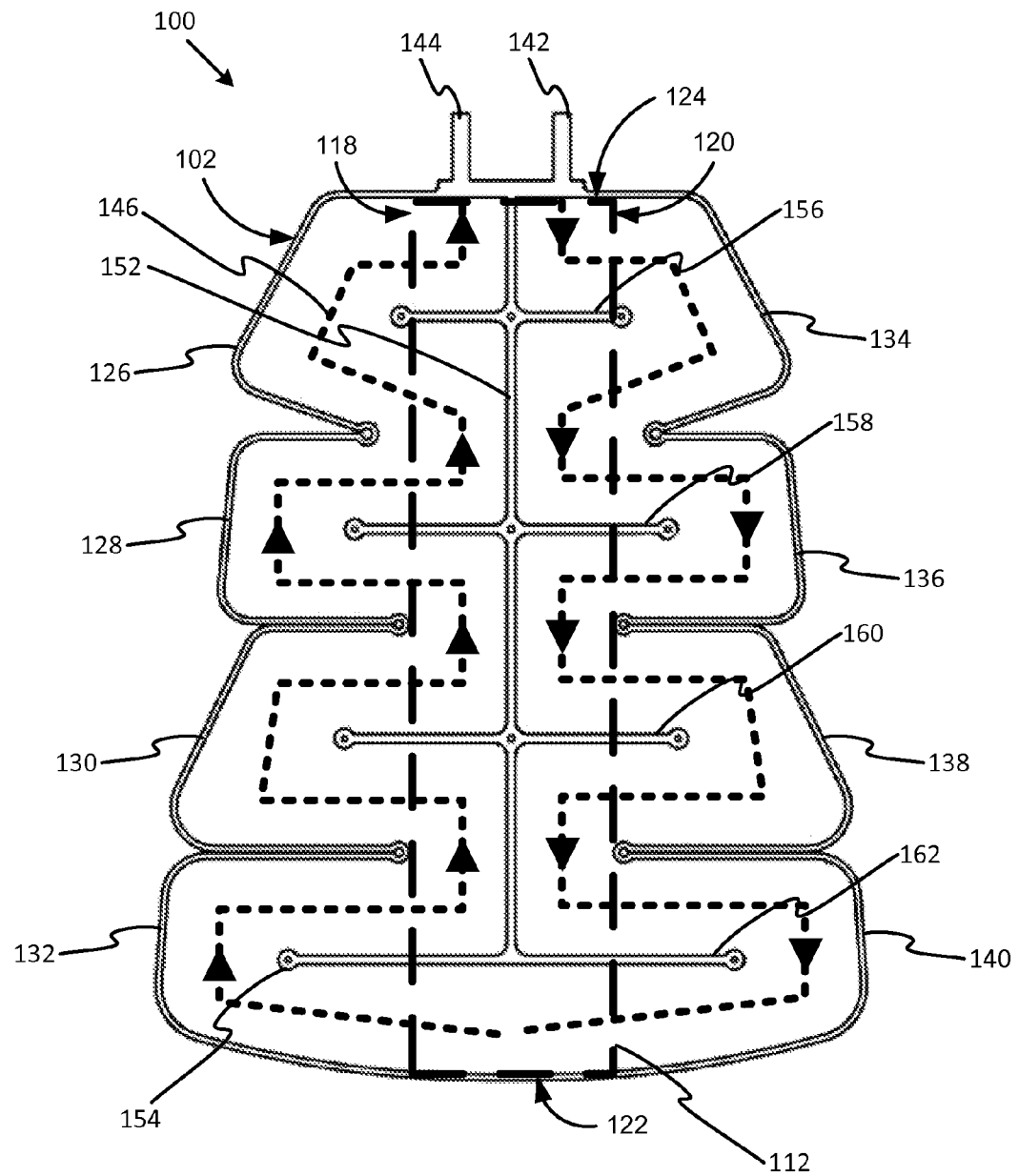
FIG. 4 is a view of an exemplary patient warming device with patient access with a fluid flow path.

As shown in FIG. 4, for example, fluid inlet 142 and outlet 144 may be located at a portion near or at the distal end 122 or near or at the proximal end 124 of the central portion 112. For example, fluid inlet 142 may be located on a first side 118, or half, of the central portion 112, and the fluid outlet 144 may be located on a second side 120, or half, of the central portion 112. Alternatively, the fluid inlet 142 and outlet 144 may be located at opposite ends. In other embodiments, the fluid inlet 142 and outlet 144 may be located adjacent or separately at any location along an outer edge, flap, or middle of the wrap 102.

The continuous fluid flow path 146 may guide the liquid 110 through the wrap 102 and substantially fill the space between the first and second compliant layers 104, 106. The fluid flow path 146 may be defined by the outer border 108 and a plurality of internal sealed connections 150 between the first and second compliant layers 104, 106. The liquid 110 may enter the fluid flow path 146 at a rate of at least about 500 mL/min (30.5 in$^3$/min) to about 800 mL/min (48.8 in$^3$/min) to deliver sufficient heat to maintain normothermia or treat hypothermia of the patient during functional use of the patient warming device. To increase heat delivery to the patient, the liquid flow rate may be increased to about 2 L/min (0.07 ft$^3$/min) or more. The desired flow rate may be adjusted by using a fluid control pump.

In some embodiments, the fluid flow path 146 may guide the liquid 110 to fill, sequentially, flaps 134, 136, 138, and 140 extending from the second side 120 of the central portion 112 and then to fill, sequentially, flaps 132, 130, 128, and 126 extending from the first side 118 of the central portion 112. As the liquid 110 travels through the wrap 102 along fluid flow path 146, the liquid 110 delivers heat to the patient through the first compliant layer 104 that is in contact with the patient's skin. Therefore, as the liquid 110 flows along the fluid flow path 146, the liquid 110 loses heat, or becomes cooler (i.e., liquid flowing through flaps 134, 136, 138, 140 is warmer than liquid flowing through flap 126, 128, 130, 132). For example, temperature of the liquid 110 at the fluid inlet 142 may decrease approximately 0.2° C. (32° F.) to 1.0° C. (34° F.) by the time it reaches the fluid outlet 144. The difference in temperature between liquid at the fluid inlet 142 and fluid outlet 144 may vary depending on the body temperature of the patient, which creates a gradient that drives heat transfer from the liquid 110 to the surface of the patient as the liquid 110 flows along the fluid flow path 146. To maximize heat delivery to the patient, flaps 134, 136, 138, 140 may fold over to directly contact the patient's skin, and flaps 126, 128, 130, 132 may fold over the flaps 134, 136, 138, 140, respectively.

The plurality of internal sealed connections 150 may be formed by RF welding, or another plastic welding technique. The sealed connections 150 may be formed as lines 152, circular dots 154, or any other shape. The sealed connections 150 may also form patterns. The liquid 110 substantially fills the space 148 and flows around the internal sealed connections 150 as it circulates along the fluid flow path 146. The internal sealed connections 150 may distribute the liquid 110 more evenly throughout the wrap 102 so as to provide a low profile patient warming device. Those of skill in the art will appreciate, in view of the present disclosure, that the flow path may take different configurations (e.g., the flow path may go first through the central portion 112, then return to the outlet 144 via paths through the flaps).

The shape, location, and/or pattern of the sealed connections 150 and the distance between the sealed connections 150 may be configured to reduce stippling and facilitate even distribution of the liquid 110 without inhibiting or overly reducing the fluid flow rate. In other words, the shapes and spacing of the sealed connections may be configured to minimize flow resistance while facilitating distribution of the liquid 110 and also reduce stippling to the patient's skin. Moreover, the sealed connections 150 may be formed in any shape and any pattern. For example, internal sealed connections 150 may be formed or patterned as circles, ovals, squares, heart shapes, star shapes, animal shapes, company or sports team logos, or any other indicia. The shape and/or pattern of the sealed connections may be chosen to appeal to the target patient, purchaser, distributor, or user.

In some embodiments, the sealed connections 150 may include circular dots 154 that are spaced at least about 3/16 inch (4.0 mm) apart, and located throughout the flaps and central portion 112 of the wrap. As shown in FIG. 4, for example, the sealed connections 150 may also include a longitudinal line 152 along a longitudinal axis of the central portion 112, and a plurality of flow directing lines 156, 158, 160 extending from the longitudinal line into the plurality of flaps. In some embodiments, the sealed connections 150 may include a line 152 that runs along a longitudinal axis of the central portion 112, and flow directing bars or lines 156, 158, 160, and 162 that intersect the line 152 and extend from the a central area of a flap on, or extending from, the first side 118 of the central portion 112 to a central area of a flap on, or extending from, the second side 120 of the central portion 112. The fluid flow path 146 may guide the liquid 110 through the fluid inlet 142, around line 156 in flap 134 and into flap 136 around line 158 and continue through the fluid flow path 146, as indicated by the arrows and winding dotted lines of FIG. 4. In this way, flow directing bars or lines 156, 158, 160, and 162 may guide or disperse the liquid 110 more evenly through each flap. Other embodiments may include additional, fewer, or different flow directing lines.

Figure 4A:
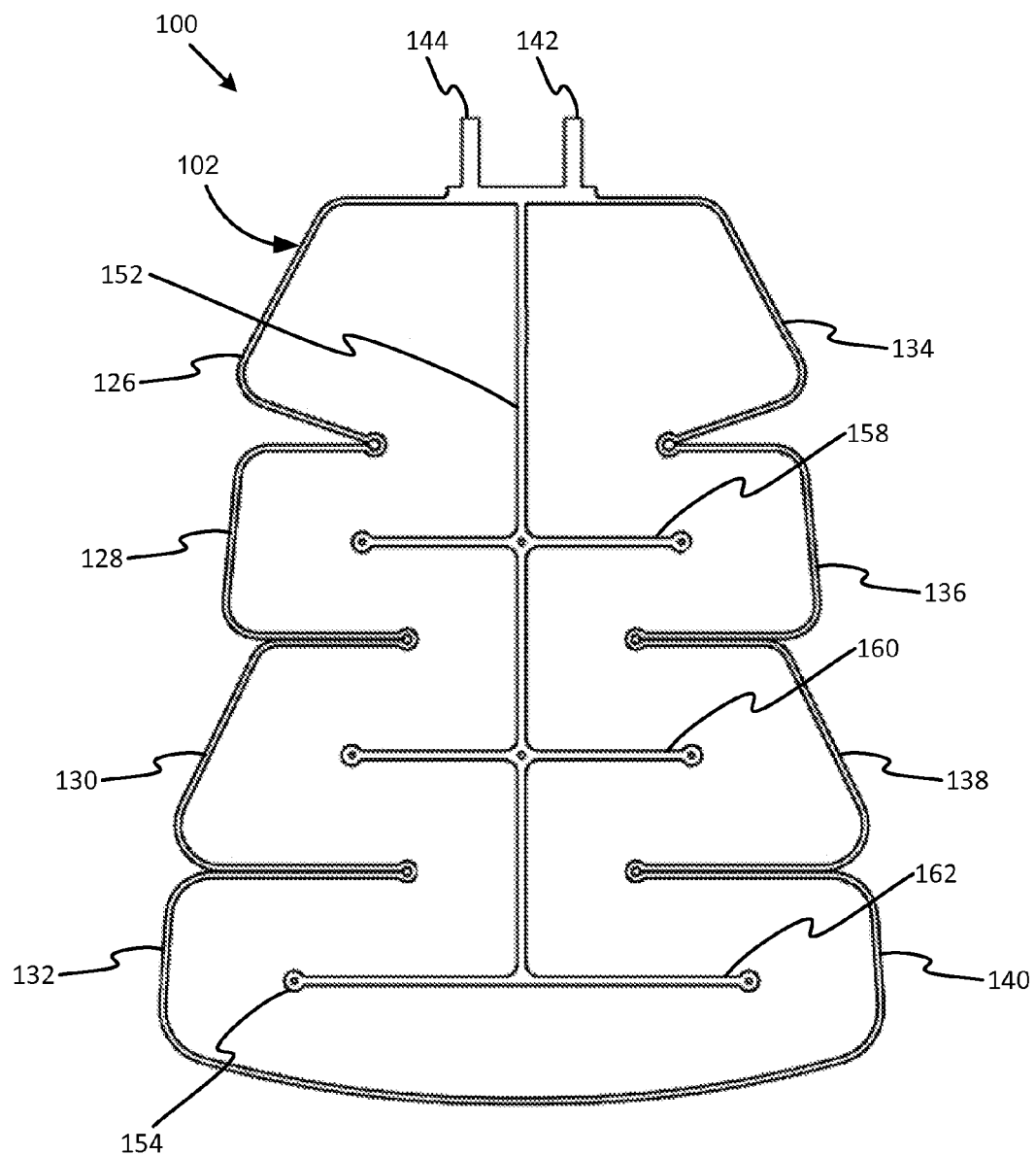
FIG. 4A is another view of an exemplary patient warming device with patient access.
Figure 5:
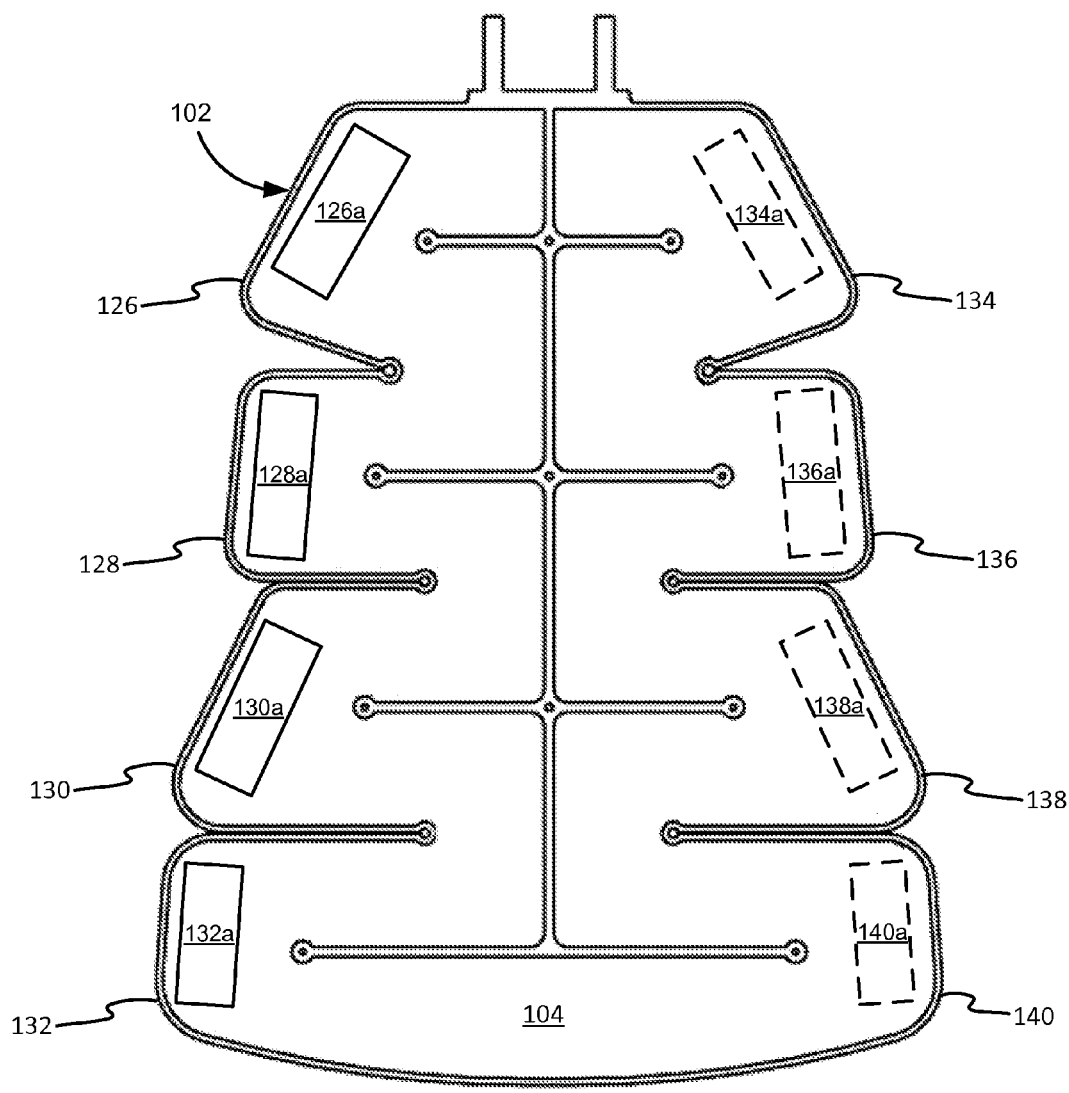
FIG. 5 is a view of an exemplary patient warming device with patient access with fasteners.

For example, as shown in FIG. 4A, flow directing bar or line 156 is removed from flaps 126, 134. Reducing the number of flow directing lines or bars, or other sealed connections, in a particular portion of the wrap 102 may decrease flow resistance in that portion of the wrap 102. For example, in some embodiments, decreased flow resistance in the flaps 126, 134 covering the patient's hand, or other body portion or appendage, may increase or speed up heat transfer to the hands, or other body portion or appendage. Flow directing lines or bars and/or other sealed connections may be arranged in any configuration or in any quantity to control, direct, or achieve desired flow conditions.

Lines 152, 156, 158, 160, and 162 may end in sealed connections shaped as circular dots 154 so as to decrease flow resistance. The corners of the flaps and intersections of lines 152, 156, 158, 160, and 162 may also be rounded so as to facilitate even distribution of the liquid 110 into the corners and to decrease flow resistance. Rounded corners may also improve comfort and feel of the patient warming device when worn by the patient. Those of skill in the art, when informed by the present disclosure, will appreciate that different flow paths (differing with respect to directionality, liquid volume and flow rate, etc.) may be provided by modifying the position, number, and/or distribution, frequency, or density of internal sealed connections.

In some embodiments, hook and loop fasteners may be used to prompt a user as to the appropriate placement of the flaps so as to maximize heat delivery. For example, as illustrated with reference to FIG. 5, the hooks or loops 134a, 136a, 138a, 140a may be arranged on the second compliant layer 106 of flaps 134, 136, 138, 140; and the corresponding hooks or loops 126a, 128a, 130a, 132a may be arranged on the first compliant layer 104 of flaps 126, 128, 130, 132 so that when the flaps are fastened, flaps 126, 128, 130, 132 overlap flaps 134, 136, 138, 140, which are in contact with the patient's skin. Alternatively, the hooks or loops 134a, 136a, 138a, 140a may be arrange on either or both of the first and second compliant layers 104, 106 of flaps 134, 136, 138, 140, in any order, such that the one or more of flaps 134, 136, 138, 140 may contact the patient's skin, and one or more of flaps 126, 128, 130, 132 may contact the patient's skin. Alternatively, straps or bands that are not integral to the wrap may be positioned around the wrap to secure the flaps and/or to provide insulation.

Figure 6:
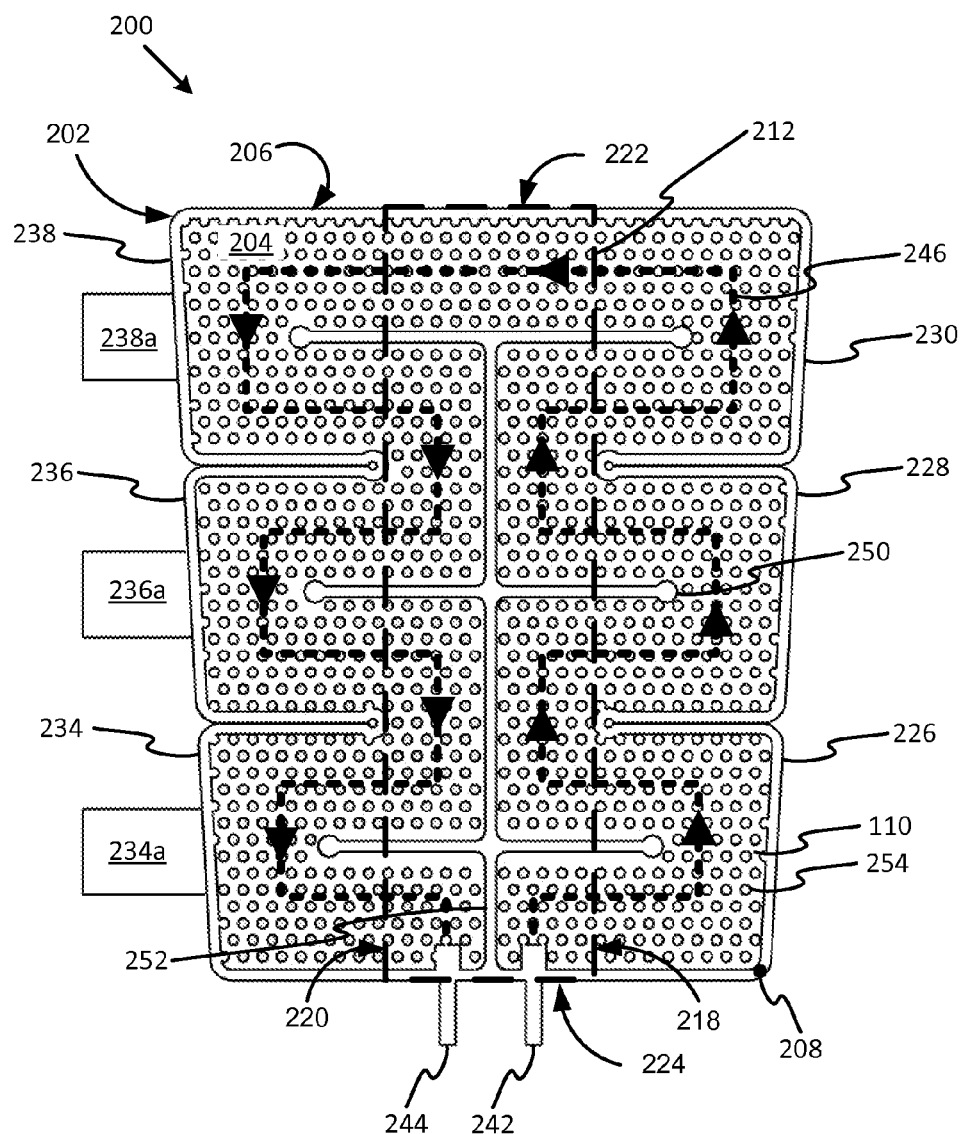
FIG. 6 is a view of an exemplary patient warming device with patient access with a fluid flow path.
Figure 7:
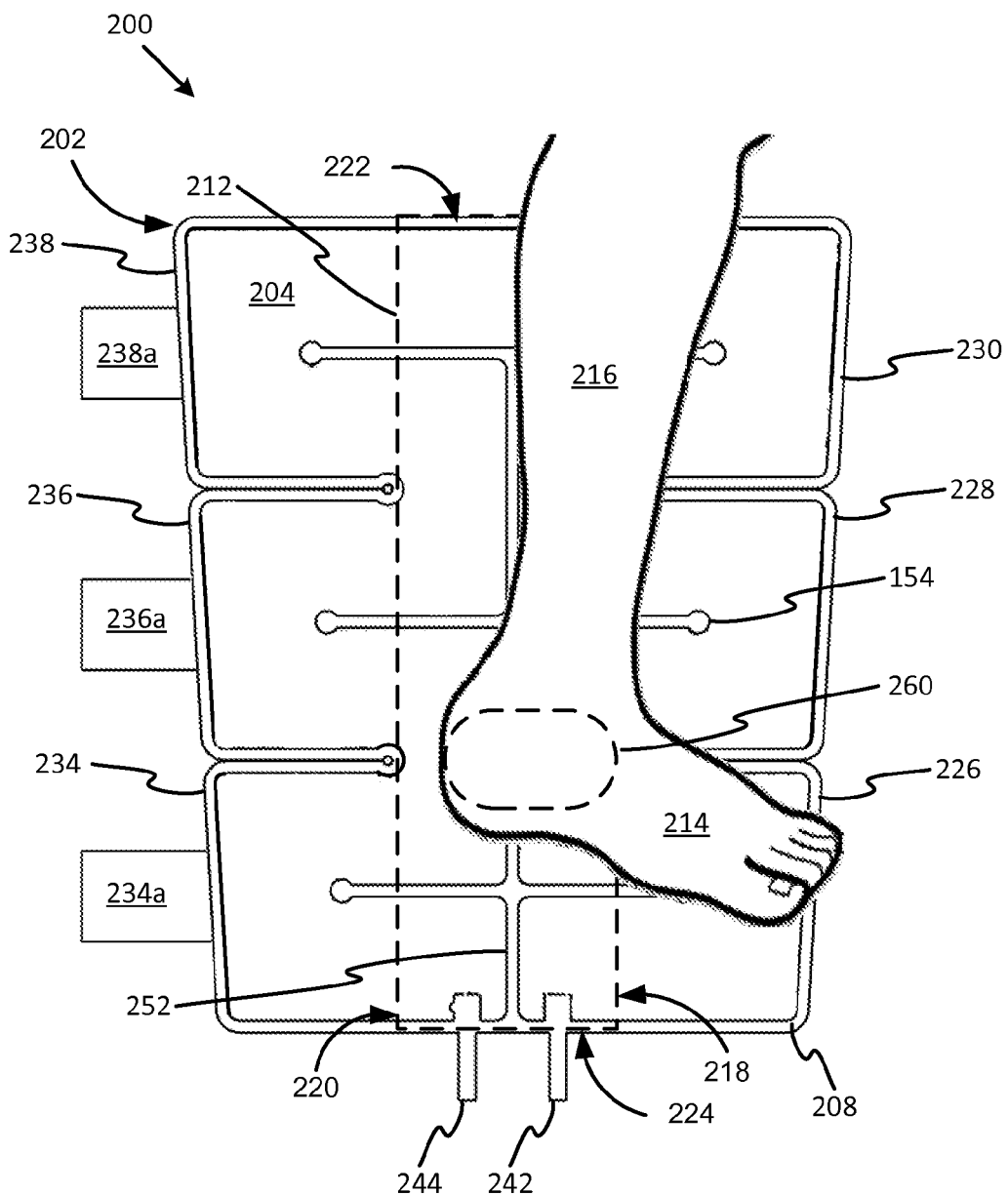
FIG. 7 is a view of an exemplary patient warming device with patient access aligned with a foot and a lower leg.

Some embodiments of a patient warming device with patient access 200 are illustrated with reference to FIG. 6. The device 200 may include a wrap 202 formed from a first compliant layer 204 and a second compliant layer 206 sealed together around an outer border 208, or outer edges, to contain a liquid 110 between the layers 204, 206. The wrap 202 may include a generally longitudinal central portion 212 that is sized to cover a surface or skin of the body portion of a patient, such as a foot 214 and/or a lower leg 216, as shown in FIG. 7, discussed below.

A plurality of flaps may extend from a first side 218 or a second side 220 of the central portion 212, or from a proximal end 222 or a distal end 224 of the central portion 212. For example, flaps 226, 228, 230 may extend from the first side 218 of the central portion 212, and flaps 234, 236, 238 may extend from the second side 220 of the central portion 212. Flaps on opposite sides of the central portion 212 may correspond in size, shape and position along the central portion 212. Alternatively, flaps extending from one side of the central portion 212, or the first side 218, may differ in size, shape, and/or position along the central portion 212 than flaps extending from an opposite side of the central portion 212, or the second side 220. In other embodiments, flaps may extend only from one side or one end of the central portion 212, or from one side and one end of the central portion 212, or any combination of sides and ends of the central portion 212. Additional, fewer, or different flaps may be included in the patient warming device 200.

Flaps extending from opposite sides of the central portion 212 may fasten to each other to surround a body portion of the patient. Alternatively, flaps may extend from one side of the central portion 212 and fasten to another side of the central portion 212. The flaps may be fastened by any suitable fastener, such as, for example, hook and loop fasteners, adhesive tabs, buttons, snaps, or press and seal fasteners.

The patient warming device 200 provides patient access to a target area of the underlying patient body surface being surrounded by the wrap 202. For example, during an operative procedure, a surgeon or other medical personnel may access a portion of the foot 214 or lower leg 216 without exposing the other portions of the underlying patient body surface. In some embodiments, the foot 214 may be accessed by unfastening, opening, or unfolding a pair of flaps 226, 234, while the other flaps remain covering the upper and lower portions of the calf and/or shin of lower leg 216 patient. Alternatively, access to the foot 214 may be provided by unfolding only one of flap 226 and/or flap 234 while the other flaps remain in contact with the patient's skin. In a similar way, access to the lower portion of the calf and/or shin may be provided by unfastening, opening, or unfolding, one or both of flaps 228, 236, access to the upper portion of the calf and/or shin may be provided by unfastening one or both of flaps 230, 238.

Providing access to a target area of the underlying patient body surface while maintaining contact with other parts of the surrounding areas increases the ability of the patient warming device 200 to maintain normothermia and/or treat hypothermia in the patient by maintaining heat transfer to body portions that remain covered. Also, by providing access to the target area while the wrap 202 remains in place, there is no need reposition or remove the patient warming device in order to introduce surgical elements, such as intravenous feed lines, pulse oximetry probes, needles, vitals monitoring instruments, or other surgical or medical instruments.

In some embodiments, liquid 110 may enter the wrap 202 through fluid inlet 242 and exit through fluid outlet 244. The liquid 110 may be a warm or heated liquid that is at a temperature between about ambient temperature, or about 20° C. (68° F.), to about 41° C. (105.8° F.). Fluid inlet 242 and outlet 244 may include flexible or rigid tubes, such as PVC, urethane, polyurethane, PE, EVA, EVA/PE blends or copolymers, SBC, medical elastomers, olefin-based compounds, ABS, polycarbonate. A fluid control pump may be connected to fluid inlet 242 to pump the liquid 110 through a continuous fluid flow path 246. The fluid inlet 242 and fluid outlet 244 may be located on the same or separate sides or ends of the wrap 202.

For example, fluid inlet 242 and outlet 244 may be located at a portion near or at the distal end 222 or near or at the proximal end 224 of the central portion 212. For example, fluid inlet 242 may be located on a first side 218, or half, of the central portion 212, and the fluid outlet 244 may be located on a second side 220, or half, of the central portion 212. Alternatively, the fluid inlet 242 and outlet 244 may be located at opposite ends. In other embodiments, the fluid inlet 242 and outlet 244 may be located adjacent or separately at any location along an outer edge, flap, or middle of the wrap 202.

The continuous fluid flow path 246 may guide the liquid 110 through the wrap 202 and substantially fill the space between the first and second compliant layers 204, 206. The fluid flow path 246 may be defined by the outer border 208 and a plurality of internal sealed connections 250 between the first and second compliant layers 204, 206. The liquid 110 may enter the fluid flow path 246 at a rate of at least about 500 mL/min (30.5 in$^3$/min) to about 800 mL/min (48.8 in$^3$/min) to deliver sufficient heat to maintain normothermia and/or treat hypothermia in the patient during functional use of the patient warming device. To increase heat delivery to the patient, the liquid flow rate may be increased to about 2 L/min (0.07 ft$^3$/min) or more. The desired flow rate may be adjusted by using a fluid control pump.

The patient warming device 200 may include fastener tabs 234a, 236a, 238a extending from flaps 234, 236, 238, respectively. The fastener tabs may be, for example, adhesive tabs, hook and loop fasteners, or other fastener that removably attaches to the second compliant layer 206 of flaps 226, 228, 230. The fastener tabs 234a, 236a, 238a and corresponding flaps 234, 236, 238 may correspond with flaps 226, 228, 230 in size, shape, and/or location along the central portion 212. Alternatively, the 234a, 236a, 238a and corresponding flaps 234, 236, 238 may vary in size, shape, and/or location along the central portion 212 without corresponding with flaps 226, 228, 230 in size, shape, and/or location along the central portion 212.

In other embodiments, the patient warming device with patient access may include any number of flaps and fasteners. The fasteners may include any suitable fasteners, including, for example, hook and loop fasteners, adhesive tabs, buttons, snaps, or press and seal fasteners, or any combination thereof. The fasteners may be located anywhere on the flaps, such as on the first compliant layer or the second compliant layer, or on the central portion of the wrap. Fasteners may be located on one or more, or all, of the flaps.

In some embodiments, as illustrated with reference to FIG. 7, the wrap 202 is used to cover a foot 214 and lower leg 216, the flaps 226, 234 located at or near the distal end 224 may extend a shorter distance from the central portion 212 than flaps 230, 238 located at or near the proximal end 222 of the central portion 212. Flaps 226, 234 may be configured (e.g., sized, shaped, tapered, and/or contoured) to fold over and cover the foot 214, flaps 228, 236 configured to fold over and cover a portion of the calf and shin of lower leg 216 nearest the foot, and flaps 230, 238 configured to fold over and cover an upper portion of the calf and shin of lower leg 216 nearest the knee. Flaps 226, 228, 230 may extend a predetermined distance from the central portion 212 so as to completely overlap or partially overlap with flaps 234, 236, 238. Alternatively, flaps 226, 228, 230 and flaps 234, 236, 238 may fold over to cover a body portion without overlapping another flap. Although the patient warming device 200 is described here for use with a foot 214 and lower leg 216, the device 200 may be configured (e.g., sized, shaped, tapered, and/or contoured) to surround any other body portion or appendage of a patient.

The patient warming device 200 may include a sealed border defining an opening 260 that is configured to fit a heel of the foot 214. For example, the opening 260 may be sized and located on the central portion 212 so that the heel may rest in the opening 260, thereby exposing and relieving pressure to the heel of the foot 214. The patient warming device 200 may include additional, different, or fewer openings configured to fit any body portion or appendage of the patient.

Figure 8:
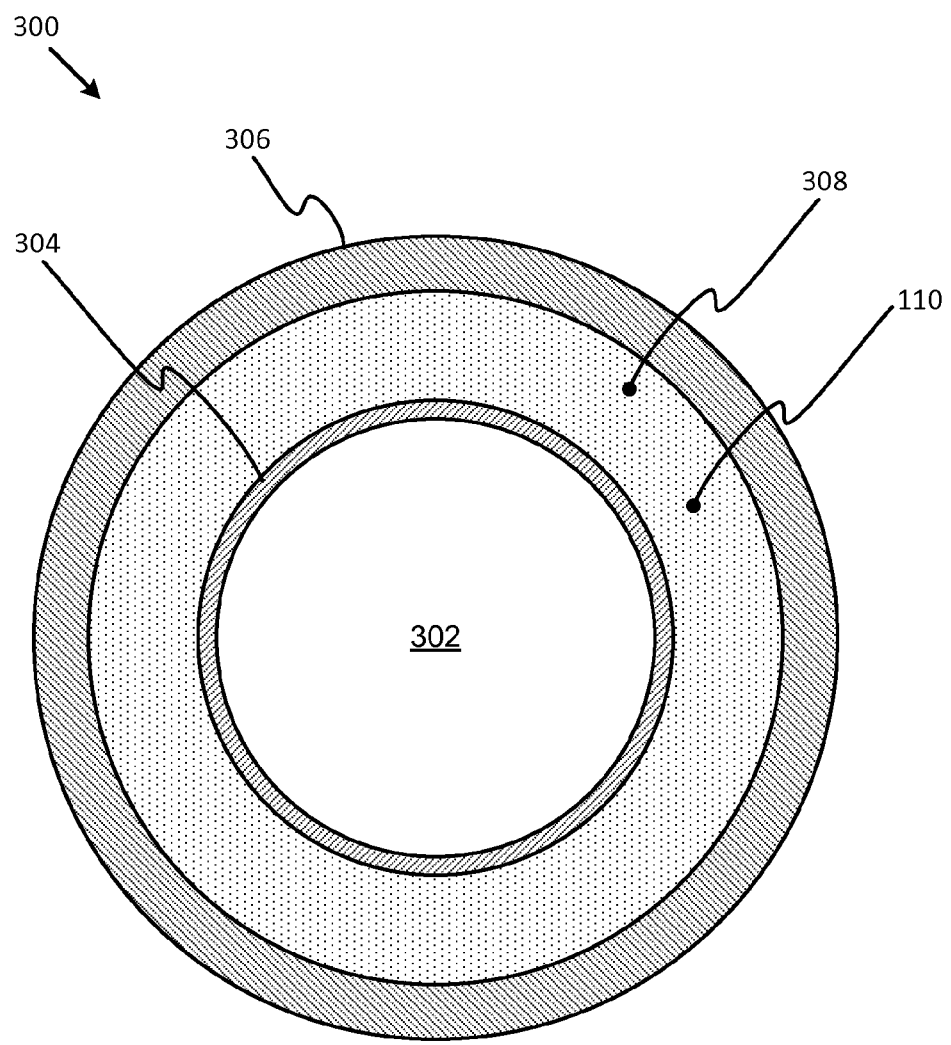
FIG. 8 is a diagrammatic view of a cross-section of an exemplary compressive patient warming device.

In some embodiments, as illustrated diagrammatically with reference to FIG. 8, a compressive patient warming device 300 simultaneously delivers heat and applies a compressive load to an appendage 302, or body portion, of a patient by surrounding the appendage, or body portion, with an elastic inner layer 304 and an outer layer 306 that is attached to and covers the inner layer. The outer layer 306 may be an insulating material such as a foam, gel, or insulative fabric. The elastic inner layer 304 conforms snugly to the shape of the appendage.

The elastic inner layer 304 may be a tight fitting wrap, sleeve, or garment that wraps around, or surrounds, and contacts substantially most, or substantially all, of an underlying surface area of the appendage 302 to maximize heat transfer to the patient. For example, at least about 90% to about 95% of the surface area of the elastic inner layer 304 contacts the patient's skin. The elastic inner layer 304 may be an elastic material that is sufficiently strong to apply a compressive force on the surrounded appendage, or body portion, so as to compress surface veins, arteries, and muscles, increasing venous blood flow velocity and valve effectiveness. The outer layer 306 may be an elastic material or a rigid material. When the device is wrapped around the patient appendage 302, or body portion, the inner layer 304 is substantially entirely, or at least partially, concentric with the outer layer 306.

A space 308 between the inner and outer layers 304, 306 holds a heat transfer medium, or liquid, 110 that delivers heat to the patient through the inner layer 304, while the compressive patient warming device 300 is wrapped around the appendage 302. The heat transfer medium, or liquid, 110 may fill substantially all, e.g., about 90% to 95% or more, of the space between the inner layer 304 and the outer layer 306 and distribute heat generally across the surface of the underlying surface area of the patient's skin. Alternatively, the heat transfer medium 304 may partially fill the space between the inner layer 304 and outer layer 306 so as to deliver heat to a localized area of the underlying surface area. In other embodiments, heat may be applied to a localized heat source may be applied at a section of the inner layer that covers an area of high venous density, or any other desired area.

Figure 9:
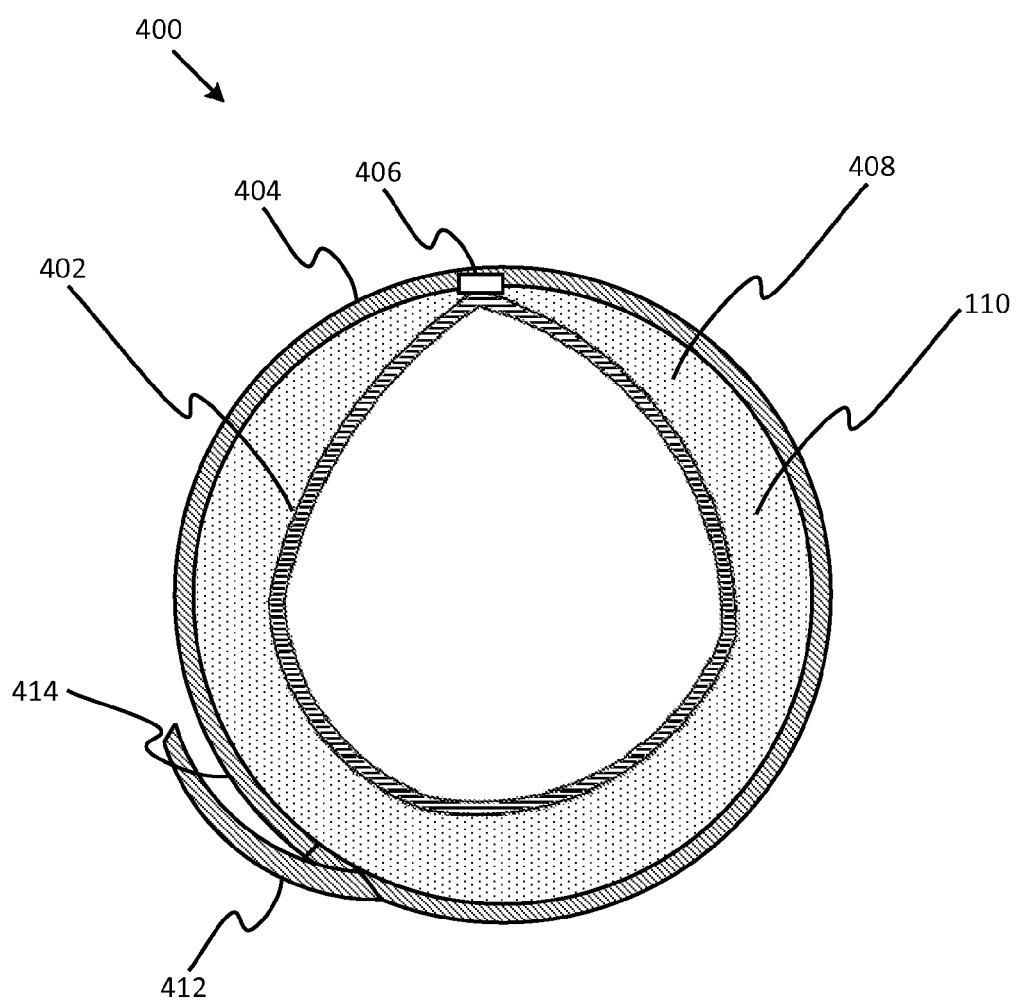
FIG. 9 is a diagrammatic view of a cross-section of an exemplary compressive patient warming device.

In some embodiments, as illustrated with reference to FIG. 9, a compressive patient warming device 400 simultaneously delivers heat and applies a compressive load to an appendage, or body portion, of a patient by surrounding the appendage, or body portion, with an elastic inner layer 402 and an outer layer 404 that is attached at a connection 406 to the inner layer 402. The patient warming device 400 includes a space 408 between the inner and outer layers 402, 404 that is substantially filled with a heat transfer medium 110. The patient warming device 400 may include additional connections between the inner and outer layers 402, 404. The outer layer 404 may include a tab 412 for fastening, tightening or adjusting the outer layer 404 around the appendage, or body portion. The tab 412 may attach to an external surface 414 of the outer layer 404, such as by using a fastener, including for example, a hook and loop fastener, adhesive tabs, buttons, snaps, or press and seal fasteners.

When the outer layer 306, 404 of compressive warming device 300, 400 is a rigid material or an elastic material, a compressive load or pressure may be applied to the appendage by controlling the flow of the heat transfer medium 110 using a fluid control pump, or other controller. When the outer layer 306, 404 is an elastic material, a compressive load may be applied, additionally or alternatively, on an external surface of the outer layer 306, 404.

The heat transfer medium 110 may be one or more of a liquid, a visco-elastic foam that conforms to the appendage along with the inner layer 304, 402, or a viscous gel, sand, heat transferring beads, or any combination thereof. The inner layer 304, 402 may be a non-permeable material that holds a liquid between the inner layer 304, 402 and the outer layer 306, 404. The non-permeable material may include, for example, PVC, urethane, polyurethane, PE, EVA, EVA/PE blends or copolymers, SBC, medical elastomers, olefin-based compounds, ABS, or any combination thereof. Alternatively, the inner layer 304, 402 may be any elastic material that can hold a non-liquid heat transfer medium 110, including, for example, a viscoelastic foam, or sand. The elastic material may include, for example, cotton, polyester, nylon, rubber or any combination thereof.

Figure 10:
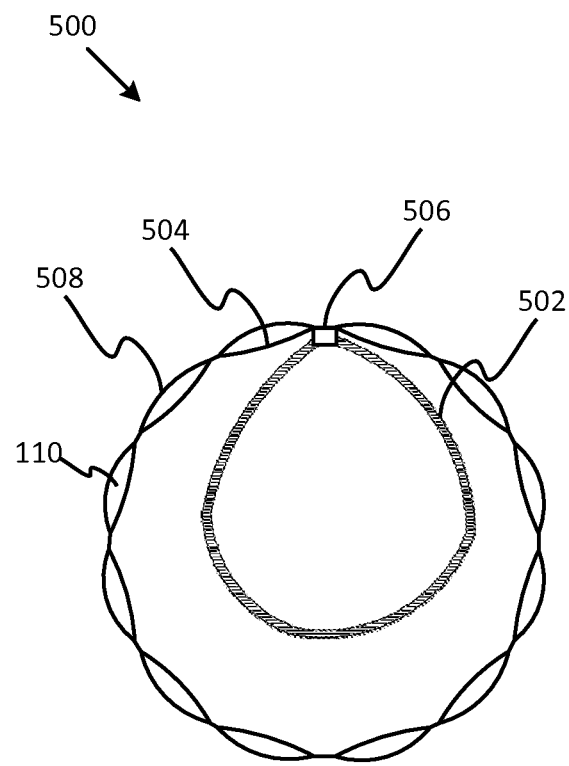
FIG. 10 is a diagrammatic view of a cross-section of an exemplary compressive patient warming device.

In some embodiments, as illustrated with reference to FIGS. 10 and 11, a compressive patient warming device 500 may include an embodiment of a patient warming device with access 100 as described above and as illustrated with respect to FIGS. 1-5, or an embodiment of a patient warming device with access 200 as described above and as illustrated with respect to FIGS. 6-7. An elastic inner layer 502 may be attached to an intermediate layer 504 at connection 506. The first compliant layer 104, 204 of a patient warming device with access 100, 200 may form the intermediate layer 504 of the compressive patient warming device 500. The second compliant layer 106, 206 of the patient warming device with access 100, 200 may form an outer layer 508 of the compressive patient warming device 500. The elastic inner layer 502 may include, for example, a compression sleeve, as shown in FIG. 10. The connection 506 may include, for example, hook and loop fasteners, adhesive tabs, buttons, snaps, or press and seal fasteners.

Figure 11:
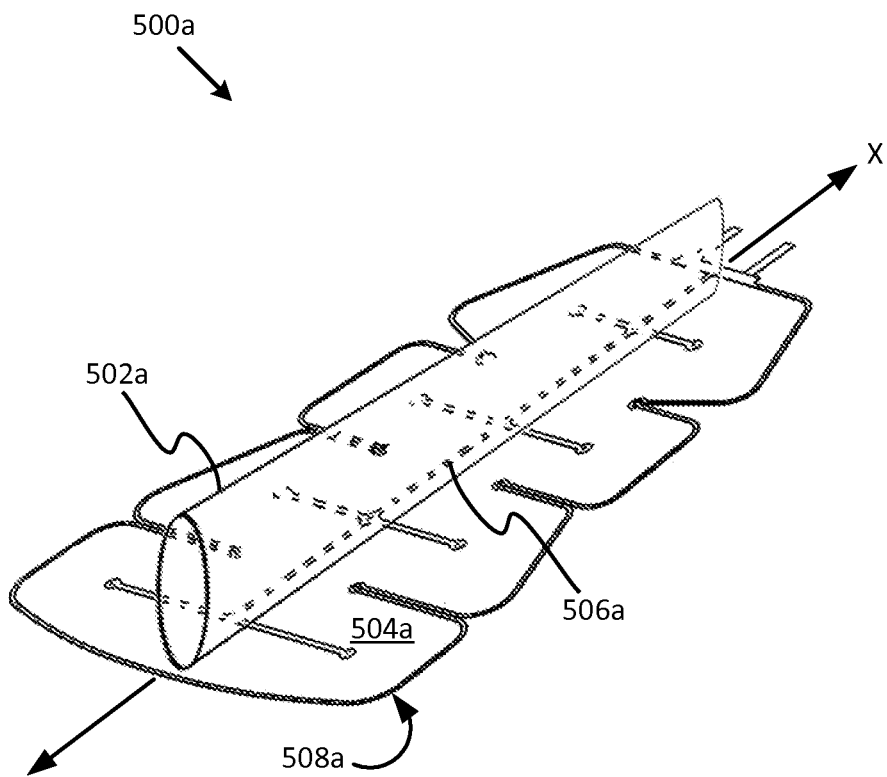
FIG. 11 is a view of an exemplary compressive patient warming device.

As shown in FIG. 11, for example, the elastic inner layer 502a may be attached to the intermediate layer 504a at connection 506a along a longitudinal axis X of the central portion 112, 212 of the patient warming device 100, 200. The elastic inner layer 502a may include, for example, a compression sleeve, as shown in FIG. 11. A compressive load may be applied through the compressive patient warming device 500a by controlling the flow of the liquid 110 through the fluid flow path 146, 246, for example, by using a fluid control pump. When the wrap 102, 202 is in functional use, surrounding the body portion, or appendage, the liquid 110 is directed through the fluid flow path 146, 246, the wrap 102, 202 is inflated and the liquid 110 exerts a compressive load through the first compliant layer 104, 204 on the underlying body portion, or appendage. The second compliant layer 106, 206 of the patient warming device with access 100, 200 may form an outer layer 508a of the compressive patient warming device 500a.

Figure 12:
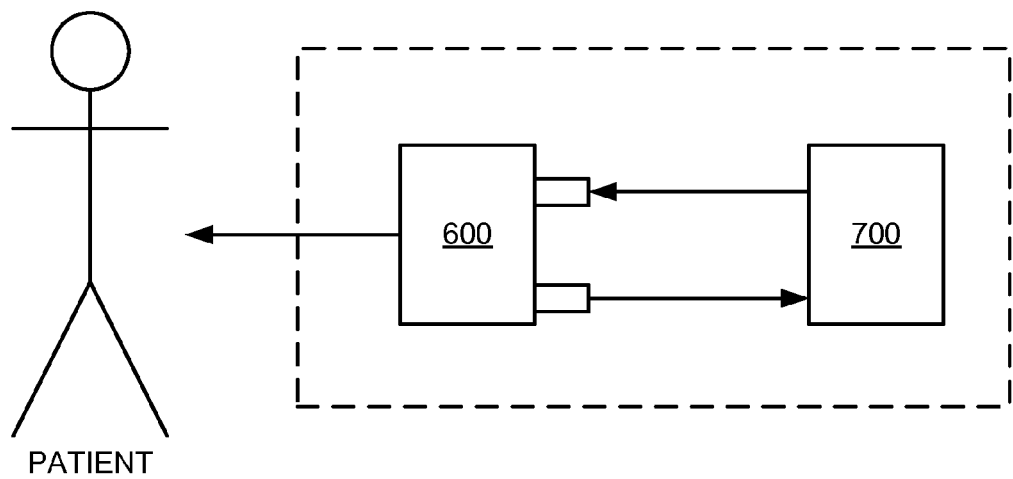
FIG. 12 is a system diagram of an exemplary patient warming and DVT prevention system.

In some embodiments, as illustrated with reference to FIG. 12, a patient warming and deep vein thrombosis prevention system includes a patient warming device 600 and a fluid control pump 700. The fluid control pump 700 circulates a heat transfer medium to the patient warming device 600, which delivers heat to the patient across the surface area of the patient warming device 600. The heat transfer medium may include, for example, a warm liquid, such as water or other aqueous liquids, a viscous gel, a hydrogel, an organic liquid (e.g., oil or oil-based liquid, or any other organic liquid or flowable material with a heat capacity suitable for effective use in keeping with the principles of the present disclosure), a synthetic oil, a foam, or forced air, or any combination thereof. The heat transfer medium is cooled as heat is delivered to the patient, and pumped out of the patient warming device 600 by the control pump 700. Alternatively, or additionally, the cooled fluid may exit the patient warming device 600 through another mechanism, such as a vacuum, suction, or drain.

Figure 13:
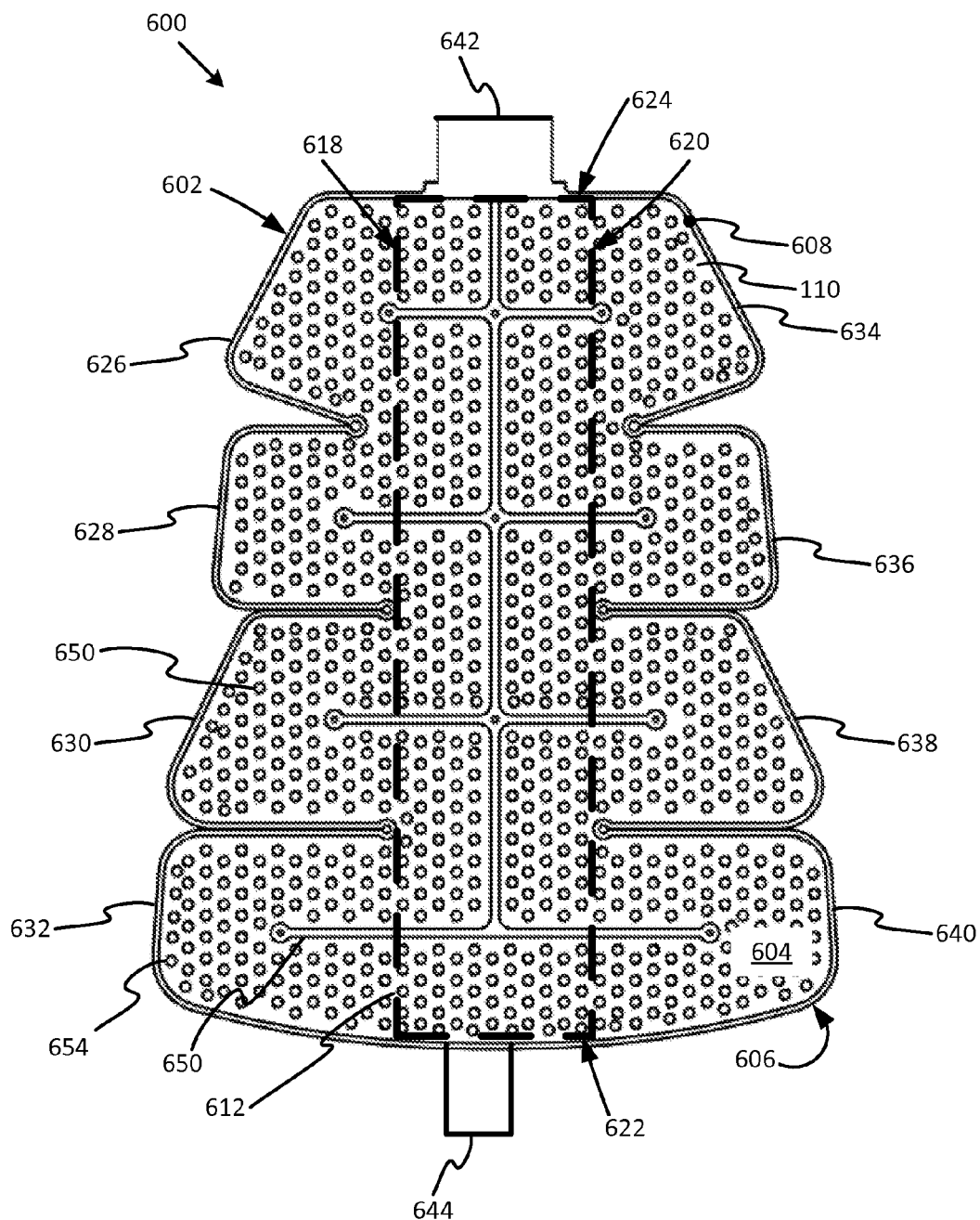
FIG. 13 is a view of an exemplary patient warming device in a patient warming and DVT prevention system.

In some embodiments, as illustrated with reference to FIG. 13, patient warming device 600 may include a wrap 602 formed from a first compliant layer 604 and a second compliant layer 606 sealed together around an outer border 608, or outer edges, to contain a liquid 110 between the layers 604, 606. The first and second layers 604, 606 may be sealed around the border 608, for example, by radio frequency (RF) welding, so as to contain the liquid 110. The first compliant layer 604 may be configured to contact the skin of the patient, and the second compliant layer 606 may face away from the skin, or be exposed to the surrounding environment. The wrap 602 may include a generally longitudinal central portion 612 that is sized to cover a surface or skin of the body portion of a patient. The central portion 612 has a first side 618 and a second side 620, and a proximal end 622 and a distal end 624.

A plurality of flaps 626, 628, 630, 632, 634, 636, 638, 640 extend from opposite sides of the central portion 612. One or more flaps from opposite sides fasten to each other to surround the body portion. During functional use, the flaps 626, 628, 630, 632, 634, 636, 638, 640 are openable to provide access to an underlying patient body surface. The liquid 110 enters the wrap at a fluid inlet 642 and exits at a fluid outlet 644.

Figure 14:
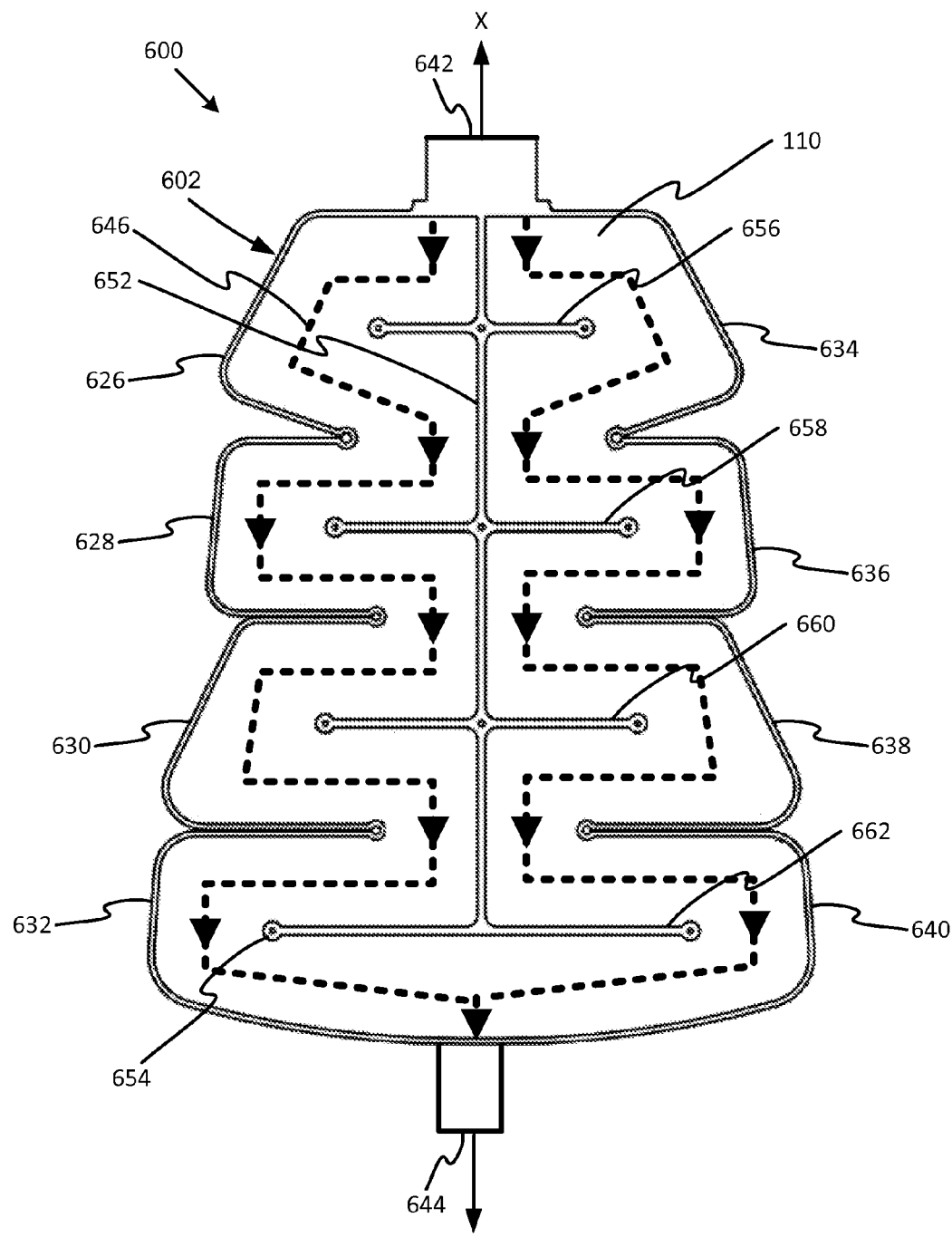
FIG. 14 is a view of a fluid flow path in an exemplary patient warming device in a patient warming and DVT prevention system.

In some embodiments, as illustrated with reference to FIG. 14, a continuous fluid flow path 646 extends between the first compliant layer 604 and the second compliant layer 606 between the fluid inlet 642 and the fluid outlet 644. The path 646 is defined by the outer border 608 and plurality of sealed connections 650 between the first and second compliant layers 604, 606. The sealed connections 650 may include a vertical line or seam 652 that runs along a longitudinal axis of the central portion 612, circular or dot shaped seams 654, and transverse seams, or flow directing lines or bars, 656, 658, 660, 662 that intersect the vertical seam 652. Alternatively, or additionally, the sealed connections 650 may include lines and dots arranged in any other patterns or locations within the outer borders.

The fluid control pump 700 is attached to the fluid inlet 642 and pumps liquid 110 into the fluid flow path 646 to fill the wrap 602. As the wrap 602 is being filled, the liquid 110 simultaneously applies pressure and delivers heat to the body portion being surrounded by the wrap 602. The fluid control pump 700 controls fluid flow rate to the wrap 602 and fills the wrap 602 sufficiently full to exert surface pressure on the patient. The pressure provided is generally effective to prevent deep vein thrombosis. For example, the fluid control pump 700 may alternate the fluid flow rate between a higher flow rate of about 3 L/min (0.11 ft$^3$/min) and a lower flow rate of about 500 mL/min (30.5 in$^3$/min). The fluid flow rate may exert a pressure, or a compressive load, on the underlying surface area that is between about 15 mmHg (2.0 kpa) and 100 mmHg (13.33 kpa). Alternatively the fluid control pump 700 may vary the flow rate to any appropriate flow rate effective to maintain normothermia and prevent deep vein thrombosis. The necessary flow rate may be determined based on environmental factors, such as ambient temperature (e.g., temperature of the surrounding environment), air pressure, patient body temperature, type of fluid being controlled, size and material of the wrap, the fluid flow path, the body portion or appendage being surrounded, and other factors that would be apparent to one of skill in the art.

In some embodiments, a patient warming and DVT prevention system may include sensors to monitor temperature and pressure applied at the surface of the appendage or body portion. For example, sensors may be placed on the underlying surface of the patient body portion or appendage to be surrounded by the patient warming device 600. The sensors may be coupled to a system controller, such as the fluid control pump 700. As the liquid 110 fills the wrap 602, the sensors may provide a feedback signal to the fluid control pump 700, which may be configured to adjust the temperature of the liquid 110 entering the fluid inlet 642 so as to maintain the temperature of the underlying surface within a predetermined range to maintain normothermia. For example, the temperature of the liquid 110 may be adjusted to maintain a temperature at the heat transfer surface of between about 36° C. (96.8° F.) and 40° C. (104° F.). Alternatively, or in addition, the heat may be adjusted using the feedback system and patient core temperature monitoring.

In some embodiments, the wrap 602 of a patient warming and DVT preventions system may be worn around a patient's lower leg and foot. With reference to FIG. 14, the fluid inlet 642 is located at or near the distal end 624 of the central portion 612 and the fluid outlet 644 is locate at or near the proximal end 622 of the central portion 612. The wrap 602 may be positioned on the patient so that the fluid inlet 642 is nearer the foot of the patient and the fluid outlet 644 is nearer the heart of the patient. As the liquid 110 enters the wrap 602, the fluid flow path 646 fills the flaps sequentially beginning with flaps 626, 634 nearest the fluid inlet 642 and ending with flaps 632, 640 nearest the fluid outlet 644. Sequentially filling the wrap 602 from an end that is further from the heart to an end that is nearer to the heart may encourage or promote venous blood flow by applying pressure, such as in an upward massage motion, to the underlying body portion or appendage in the same sequence along the underlying body portion and towards the heart. The wrap 602 may be configured for use with any other body portion, or appendage, and may be aligned with the body portion, or appendage, so that the distal end or fluid inlet 642 is further from the heart than the proximal end or fluid outlet 644.

Figure 15:
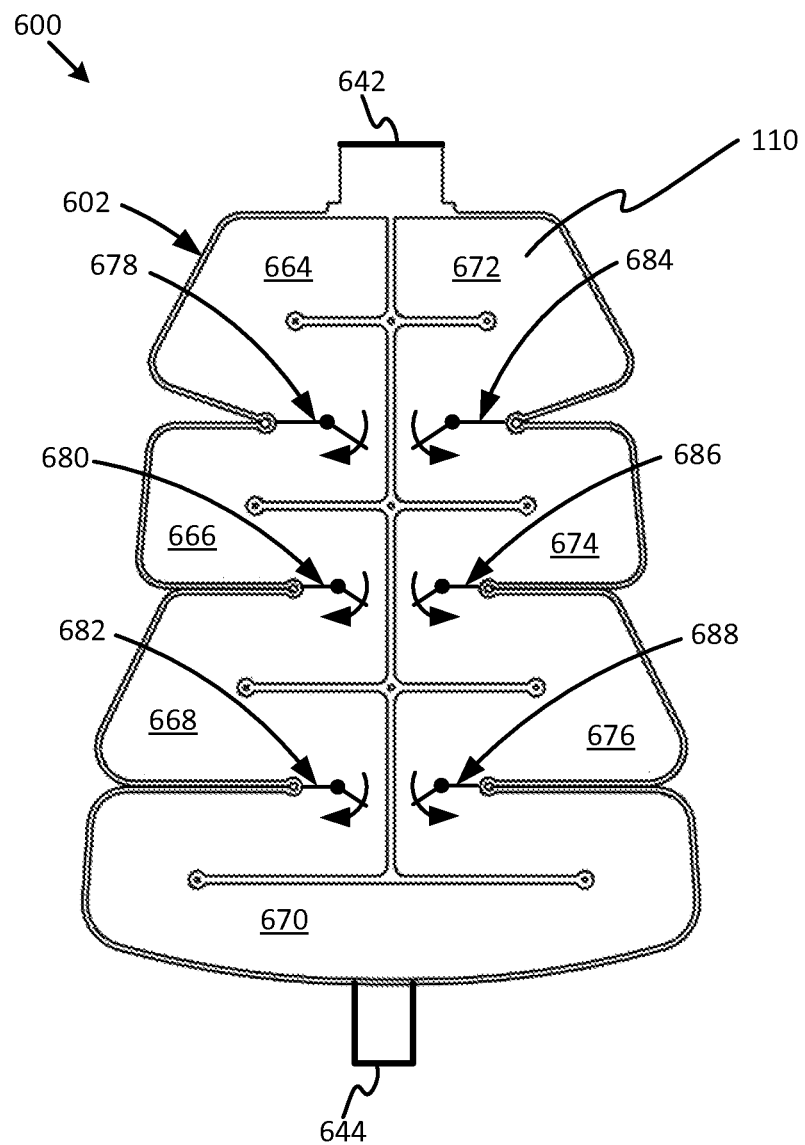
FIG. 15 is a view of an exemplary patient warming device with fluid control mechanisms in a patient warming and DVT prevention system.

In some embodiments, as illustrated with reference to FIG. 15, the wrap may include subsections 664, 666, 668, 670, 672, 674, 676 that are defined by the sealed connections 650 and outer boundaries. For example, subsection 664 may be defined by the outer border 608 of flap 626 and a sealed connection 650, such as a longitudinal line or seam 652 that lies along a longitudinal axis X of the central portion 612. The subsections 664, 666, 668, 670, 672, 674, 676 may correspond with the flaps 626, 628, 630, 632, 634, 636, 638, 640, or may be defined independently of the flaps. The subsections 664, 666, 668, 670, 672, 674, 676 may be in fluid communication, or may be physically separated by sealed connections 150. The wrap 602 may include one or more fluid control mechanisms 678, 680, 682, 684, 686, 688 positioned between two or more subsections. Alternatively, or additionally, one or more fluid control mechanisms may be located in or near the fluid inlet 642 and/or fluid outlet 644.

For example, the fluid control mechanisms 678, 680, 682, 684, 686, 688 may be positioned to join internal sealed connections with the outer boundary. Alternatively, or additionally, more or less fluid control mechanisms may be located at different locations along the fluid control path 646. The fluid control mechanisms 678, 680, 682, 684, 686, 688 may be check valves that allow fluid to flow in one direction towards the fluid outlet. Alternatively, or additionally, other types of fluid control valves may be used such as duck bill valves, bifurcating valves, or umbrella valves.

As the liquid 110 enters the wrap 602, the fluid control mechanisms 678, 684 may allow the subsections 664, 672 nearest the fluid inlet 642 to be filled sufficiently to exert a surface pressure onto the patient. Then the next subsections 666, 674, and the next subsections 668, 676, and subsection 670, may be filled in sequence until each subsection is sufficiently full to exert a surface pressure onto the patient. The wrap 602 may be applied to patient body portion, or appendage, so that the fluid inlet 642 corresponds to a location on the patient that is further from the heart, and the fluid outlet 644 corresponds to a location on the patient that is closer to the heart. As such, the sequential filling of the subsections, from those further from the heart, to those closer to the heart, may encourage or promote venous blood flow and effectively prevent DVT.

As another example, the fluid control mechanisms may be a plurality of closely spaced sealed connections between the first and second compliant layers. The closely spaced sealed connections (e.g., less than 3/16 inch (4.0 mm) apart may create localized areas of increase flow resistance, so as to decrease the fluid flow rate in those areas. The fluid control mechanisms may be configured to allow liquid to fill a first section sufficiently full to exert surface pressure onto the patient before filling a next section. For example, fluid control mechanisms 678 and 684 may decrease or stop fluid flow into subsections 666 and 674 until subsections 664 and 672 are sufficiently full to exert surface pressure onto the patient. In this way, fluid control mechanisms may be configured to allow the subsections to be sequentially filled from the distal end 624 of the central portion 612 to the proximal end 622 of the central portion 612. Sequentially filling the subsections provides for sequential compression of the underlying surface of the patient so as to promote venous blood flow, and prevent deep vein thrombosis.

Figure 16:
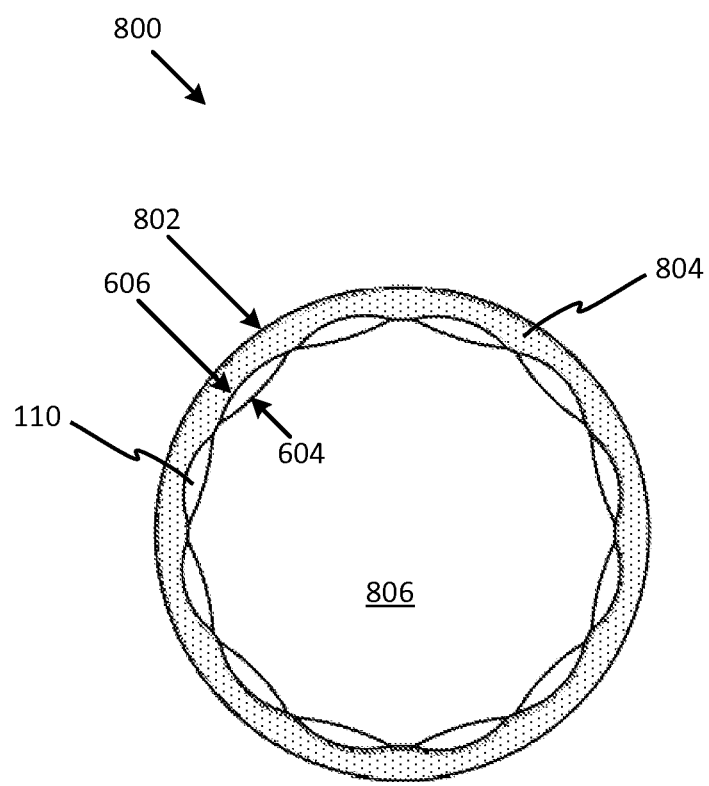
FIG. 16 is a view of a diagrammatic view of a cross-section of an exemplary patient warming device in a patient warming and DVT prevention system.

In some embodiments, as illustrated with respect to FIG. 16, a patient warming and DVT prevention system 800 includes a wrap 602, having first and second compliant layers 604, 606. FIG. 16 shows a cross-sectional view of the patient warming and DVT prevention system 800. The system 800 further includes a third compliant layer 802 that is adjoining, or sealed together around the outer edge 608 of, the second compliant layer 604 so as to form an inflatable layer 804 between the two layers. When the wrap 602 is worn around a patient body portion or appendage 806, the third compliant layer 802 surrounds the second compliant layer 606, and the first compliant layer 604, so that the inflatable layer 804 applies pressure to the body portion or appendage 806 by compressing the first and second compliant layers 604, 606 and the liquid 110 between the first and second layers 604, 606. An air pump or blower may be coupled with an inlet of the inflatable layer so as to inflate the layer and apply additional surface pressure on the body portion, or appendage. The air pump or blower may also be configured to vary the air flow rate, such as between a higher flow rate and a lower flow rate, or between a positive flow rate and a vacuum mode, so as to apply an intermittent pressure on the body portion.

In other embodiments, the patient warming and DVT prevention system may include a patient warming device that includes flaps extending from one or more sides of the central portion, or from one or more ends of the central portion. The number of flaps may vary. Flaps from opposite sides or ends of the central portion may fasten together to surround the body portion or appendage of the patient. Alternatively, flaps may extend from one side or end of the central portion and fasten to another side or end of the central portion.

The following variations may apply to any embodiments of the patient warming device with access, the compressive patient warming device, the patient warming and DVT prevention system, or associated methods disclosed herein. Embodiments of the patient warming device with access, the compressive patient warming device, the patient warming and DVT prevention system, or associated methods disclosed herein, may apply to any body portion, appendage, or extremity of a patient, and may be used during in an operating or surgical environment, or in other environments.

In embodiments including flaps that extend from one or more sides or ends of a generally longitudinal central portion, the flaps may vary in number, size, shape, or location along the central portion, depending on the body portion or appendage to be surrounded, and the intended functional use. The flaps may be positioned and/or configured to allow access to the underlying surface of any surrounded patient body portion or appendage, so as to maintain normothermia and/or treat hypothermia without requiring removal or repositioning of the device. Any suitable fastening mechanisms may be used to secure the device around the patient's body portion or appendage. For example, fasteners may include, for example, hook and loop fasteners, adhesive tabs, buttons, snaps, or press and seal fasteners.

In some embodiments, the first compliant layer makes contact with the patient's skin, and the second compliant layer is exposed to the surrounding environment. The first compliant layer may have a thickness that is less than the thickness of the second compliant layer, so as to provide more efficient heat transfer to the patient. The first and second compliant layers may be welded together using any appropriate technique, including, for example, plastic welding techniques, such as radio frequency welding, hot gas welding, head sealers, speed tip welding, contact welding, hot plate welding, ultrasonic welding, friction welding, and laser welding, or any combination thereof. The first and second compliant layers may alternatively be adhesively bonded. The first and second compliant layers may be the same or different materials, and may have the same or different thicknesses.

Materials for the first and second compliant layers may include, for example, PVC, urethane, polyurethane, polyethylene (PE), EVA, EVA/PE blends or copolymers, styrenic block copolymers (SBC), medical elastomers, olefin-based compounds, ABS, or any combination thereof. Generally, the materials used may vary depending on the intended functional use, such as for average patients or patients with specific conditions or requiring special considerations (e.g., elderly, diabetic, infant, patients with allergies and/or hypersensitivity).

The liquid used in the devices and methods may be water or other aqueous liquids, a viscous gel, a hydrogel, an organic liquid (e.g., oil or oil-based liquid, or any other organic liquid or flowable material with a heat capacity suitable for effective use in keeping with the principles of the present disclosure), a synthetic oil, a foam, or any combination thereof, or any other liquid that is suitable for heat transfer. Alternatively, other heat transfer mediums may be inserted between the first and second compliant layers, such as visco-elastic foam, sand, heat transferring beads, and other suitable heat transfer mediums. The liquids and other heat transfer mediums listed here are provided as examples, and are not intended as limitations. Other liquids, fluids, and heat transfer mediums may be used. The liquid, or other heat transfer medium, may circulate through the device at a temperature of about ambient temperature, or 20° C. (68° F.), to about 41° C. (105.8° F.). When the liquid is water, the flow rate through the continuous fluid flow path may be about 500 mL/min (30.5 in$^3$/min) to about 800 mL/min (48.8 in$^3$/min), or higher.

The continuous fluid flow path may guide the liquid or other heat transfer medium between the first and second compliant layers between the fluid inlet and fluid outlet in any pattern, direction, or path that allows the liquid, or other heat transfer medium, to transfer heat efficiently to the underlying surface of the patient. The fluid inlet and fluid outlet may be located together at or near the distal end or proximate end, or first or second side, of the central portion, or at any other location on the device. Alternatively, the fluid inlet and fluid outlet may be located at opposite ends or sides of the central portion, or otherwise separately located at any location on the device.

Although various embodiments of the invention have been described, it will be apparent to those of ordinary skill in the art that many more embodiments and implementations are possible that are within the scope of the invention. For instance, steps of a method as displayed in the figures or reflected in the claims do not require a specific order of execution by way they are presented, unless specified. The disclosed steps are listed as exemplary such that additional or different steps may be executed or the steps may be executed in a different order. Those of skill in the art will appreciate that embodiments not expressly illustrated herein may be practiced within the scope of the claims, including that features described herein for different embodiments may be combined with each other and/or with currently-known or future-developed technologies while remaining within the scope of the claims.

Those of skill in the art will appreciate that embodiments not expressly illustrated herein may be practiced within the scope of the claims, including that features described herein for different embodiments may be combined with each other and/or with currently-known or future-developed technologies while remaining within the scope of the claims. Although specific terms are employed herein, they are used in a generic and descriptive sense only and not for purposes of limitation unless specifically defined by context, usage, or other explicit designation. It is therefore intended that the foregoing detailed description be regarded as illustrative rather than limiting. And, it should be understood that the following claims, including all equivalents, are intended to define the spirit and scope of this invention. Furthermore, the advantages described above are not necessarily the only advantages of the invention, and it is not necessarily expected that all of the described advantages will be achieved with every embodiment. In the event of any inconsistent disclosure or definition from the present application conflicting with any document incorporated by reference, the disclosure or definition herein shall be deemed to prevail.

We claim:

1. A patient warming device with patient access comprising:
a first compliant layer and a second compliant layer sealed together around an outer border to contain a liquid therebetween and to form a wrap configured to surround, substantially cover, and conform to a body portion of a patient, the wrap comprising:
a generally longitudinal central portion sized to cover a surface of the body portion;
a plurality of flaps extending from opposite sides of the central portion, wherein one or more flaps from the opposite sides fasten to each other to surround the body portion, and wherein one of the plurality of flaps or a first pair of flaps is separately openable during functional use to provide access to a target area of the body portion;
a continuous fluid flow path extending between the first compliant layer and the second compliant layer between a fluid inlet and a fluid outlet, said path defined by the outer border and a plurality of internal sealed connections between the first and second compliant layers and said path extending through each of the plurality of flaps; and
at least one valve disposed in the continuous fluid flow path between adjacent flaps on a common side of the central portion; and
a fluid control pump comprising a pump inlet and a pump outlet, wherein the pump outlet is in fluid communication with the fluid inlet, the pump inlet is in fluid communication with the fluid outlet, and the fluid control pump is configured to heat the liquid and continuously circulate the liquid through the continuous fluid flow path in a continuous loop.

2. The patient warming device of claim 1, wherein the flaps from the opposite sides are fastened by a fastener comprising hook and loop fastener, an adhesive tab, a button, a snap, or a press and seal fastener.

3. The patient warming device of claim 1, wherein the liquid comprises water or another aqueous liquid, a viscous gel, a hydrogel, an organic liquid, a synthetic oil, a foam, or any combination thereof.

4. The patient warming device of claim 1, wherein the body portion comprises a portion of a patient's body surrounded by the wrap corresponding to about 5% to about 10% of the patient's entire external surface so as to maintain normothermia or treat hypothermia during a surgical procedure.

5. The patient warming device of claim 1, wherein the body portion to be surrounded comprises one or more of the patient's upper arm, forearm, hand, calf, shin, foot, thigh, or any combination thereof.

6. The patient warming device of claim 1, wherein the plurality of flaps comprises:
the first pair of flaps configured to, when unfastened, provide access to an upper forearm of a patient;
a second pair of flaps configured to, when unfastened, provide access to a lower forearm of a patient;
a third pair of flaps configured to, when unfastened, provide access to an upper portion of a hand of a patient; and
a fourth pair of flaps configured to, when unfastened, provide access to fingers of a patient.

7. The patient warming device of claim 6, wherein the fourth pair of flaps is tapered from a wider portion positioned near the upper portion of the hand to a narrower portion near tips of the fingers.

8. The patient warming device of claim 1, wherein the patient warming device further comprises an opening configured to fit a heel of a patient and the plurality of flaps comprises:
the first pair of flaps configured to, when unfastened, provide access to an upper portion of a calf or shin of a patient;
second pair of flaps configured to, when unfastened, provide access to a lower portion of the calf or shin of a patient; and
a third pair of flaps configured to, when unfastened, provide access to a foot of a patient.

9. The patient warming device of claim 1, wherein the contained liquid substantially fills a space between the first compliant layer and the second compliant layer.

10. The patient warming device of claim 1, wherein:
the first compliant layer is configured to make skin contact with the body portion;
the second compliant layer is configured to face away from the skin of the body portion; and
the first compliant layer has a thickness that is approximately 50% of a thickness of the second compliant layer.

11. The patient warming device of claim 1, wherein the fluid control pump is configured to pump the liquid into the device to achieve a fluid flow rate of at least 800 ml/min within the wrap.

12. The patient warming device of claim 1, wherein:
the fluid inlet is located on a distal portion of a first side of the central portion and the fluid flow path guides the liquid through flaps extending from the first side of the central portion; and
the fluid outlet is located on a distal portion of a second side of the central portion and the fluid flow path guides the liquid from the flaps extending from the first side of the central portion to the flaps extending from the second side of the central portion and out of the device via the fluid outlet.

13. A patient warming device comprising:
a first compliant layer and a second compliant layer sealed together around an outer border to contain a liquid therebetween and to form a wrap configured to surround and conform to an appendage of a patient, the wrap comprising:
a generally longitudinal central portion sized to cover a surface of the appendage;
a continuous fluid flow path extending between the first compliant layer and the second compliant layer between a fluid inlet located at a distal end of a first side of the central portion and a fluid outlet located at a distal end of a second side of the central portion opposite the first side, said path defined by the outer border and a plurality of internal sealed connections between the first and second compliant layers;
a first set of flaps extending from the first side of the central portion, the fluid flow path leading from the fluid inlet to the first set of flaps;
at least one valve disposed in the fluid flow path between adjacent flaps of the first set of flaps;
a second set of flaps extending from the second side of the central portion, the fluid flow path leading from the first set of flaps to the second set of flaps to the fluid outlet;
a first pair of flaps comprising a flap nearest the distal end from each of the first set of flaps and the second set of flaps, the first pair of flaps extending to a first distance from the central portion;

a second pair of flaps comprising a flap nearest a proximal end of the central portion from each of the first set of flaps and the second set of flaps, the second pair of flaps extending to a second distance, greater than the first distance, from the central portion;

a plurality of hook and loop fasteners comprising:
  hook or loop components affixed to the first compliant layer of the first set of flaps; and
  corresponding hook or loop components affixed to the second compliant layer of the second set of flaps; and where the continuous fluid flow path extends through at least a plurality of the flaps; and a fluid control pump comprising a pump inlet and a pump outlet, wherein the pump outlet is in fluid communication with the fluid inlet, the pump inlet is in fluid communication with the fluid outlet, and the fluid control pump is configured to heat the liquid and continuously circulate the liquid through the continuous fluid flow path in a continuous loop.

\* \* \* \* \*